United States Patent
Chari et al.

(10) Patent No.: US 11,345,724 B2
(45) Date of Patent: May 31, 2022

(54) PROTEASOME INHIBITORS

(71) Applicant: Max-Planck-Gesellschaft zur Förderung der Wissenschaften E.V., Munich (DE)

(72) Inventors: Ashwin Chari, Göttingen (DE); Holger Stark, Waake (DE); Jil Schrader, Göttingen (DE); Fabian Henneberg, Göttingen (DE)

(73) Assignee: Max-Planck-Gesellschaft zur Förderung der Wissenschaften e.V., Munich (DE)

(*) Notice: Subject to any disclaimer, the term of this patent is extended or adjusted under 35 U.S.C. 154(b) by 142 days.

(21) Appl. No.: 16/305,693

(22) PCT Filed: Jun. 6, 2017

(86) PCT No.: PCT/EP2017/063699
§ 371 (c)(1),
(2) Date: Nov. 29, 2018

(87) PCT Pub. No.: WO2017/211818
PCT Pub. Date: Dec. 14, 2017

(65) Prior Publication Data
US 2020/0325171 A1    Oct. 15, 2020

Related U.S. Application Data

(60) Provisional application No. 62/346,203, filed on Jun. 6, 2016.

(30) Foreign Application Priority Data

Jun. 6, 2016  (EP) .................................. 16173057

(51) Int. Cl.
| | |
|---|---|
| *A61K 38/06* | (2006.01) |
| *C07K 5/083* | (2006.01) |
| *C07K 5/087* | (2006.01) |
| *C07K 5/062* | (2006.01) |
| *C07K 5/02* | (2006.01) |
| *A61K 38/00* | (2006.01) |
| *A61K 38/03* | (2006.01) |

(52) U.S. Cl.
CPC ........ *C07K 5/06069* (2013.01); *A61K 38/005* (2013.01); *A61K 38/03* (2013.01); *A61K 38/06* (2013.01); *C07K 5/0202* (2013.01); *C07K 5/081* (2013.01); *C07K 5/0806* (2013.01); *C07K 5/0808* (2013.01); *C07K 5/0812* (2013.01)

(58) Field of Classification Search
CPC ...... A61K 38/005; A61K 38/03; A61K 38/06; C07K 5/0806; C07K 5/081; C07K 5/0812
See application file for complete search history.

(56) References Cited

U.S. PATENT DOCUMENTS

| | | | |
|---|---|---|---|
| 3,592,922 | A | 7/1971 | Gier et al. |
| 4,625,066 | A | 11/1986 | Elbe |
| 2005/0143317 | A1 | 6/2005 | Abdel-Meguid et al. |
| 2009/0006002 | A1* | 1/2009 | Honisch ............... C12Q 1/6858 702/20 |
| 2010/0331326 | A1 | 12/2010 | Bock et al. |
| 2012/0165541 | A1 | 6/2012 | Albert et al. |
| 2020/0325171 | A1 | 10/2020 | Chari et al. |

FOREIGN PATENT DOCUMENTS

JP        2002145897       5/2002

OTHER PUBLICATIONS

Bahulayan et al., "An easy two step synthesis of macrocyclic peptidotriazoles via a four-component reaction and copper catalyzed intramolecular azidealkyne [3+2] click cycloaddition," Tetrahedron Letters, 53(23):2850-2855 (2012).
Bogyo et al., "Substrate binding and sequence preference of the proteasome revealed by active-site-directed affinity probes," Chemistry and Biology, 5(6):307-320 (1998).
Ei-Mostafa Azim et al., "Synthesis of 4-tert-butyl-3-(2-chloro-[2-14C]ethyl)ureido nemzene," Journal of Labelled Compounds and Radiopharmaceuticals, 39(7):559-566 (1991).
Extended European Search Report for EP Application No. 16173057.7-1453 dated Apr. 1, 2017.
Garten et al., "Inhibition of proteolytic activation of influenza virus hemagglutinin by specefic peptidyl chloroalkyl ketones," Virology, 172(1):25-31 (1989).
Gilchrist et al., "Intramolecular cycloaddition of azoalkenes derived from terminal alkenoic and alkynoic acids," Journal of the Chemical Society, 2511 (1987).

(Continued)

*Primary Examiner* — Jeffrey E. Russel
(74) *Attorney, Agent, or Firm* — Foley Hoag LLP; David P. Halstead; Lawrence P. Tardibono

(57) ABSTRACT

The present invention relates to a compound of formula (I), wherein X is C=O, C=S or B—OH; Y is an electrophile and Z is a leaving group, or Y=Z is an electrophile; $R^1$ comprises or consists of (a) (i) a first group binding to a proteolytic site of a proteasome, the first group being bound to X; and (ii) optionally a second group enhancing delivery; or (b) a group binding between subunits β1 and β2 of a proteasome; $R^2$ and $R^3$ are independently selected from H, methyl, methoxy, ethyl, ethenyl, ethynyl and cyano, wherein methyl and ethyl may be substituted with OH or halogen.

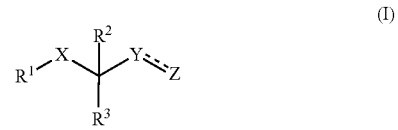

Figure 1:
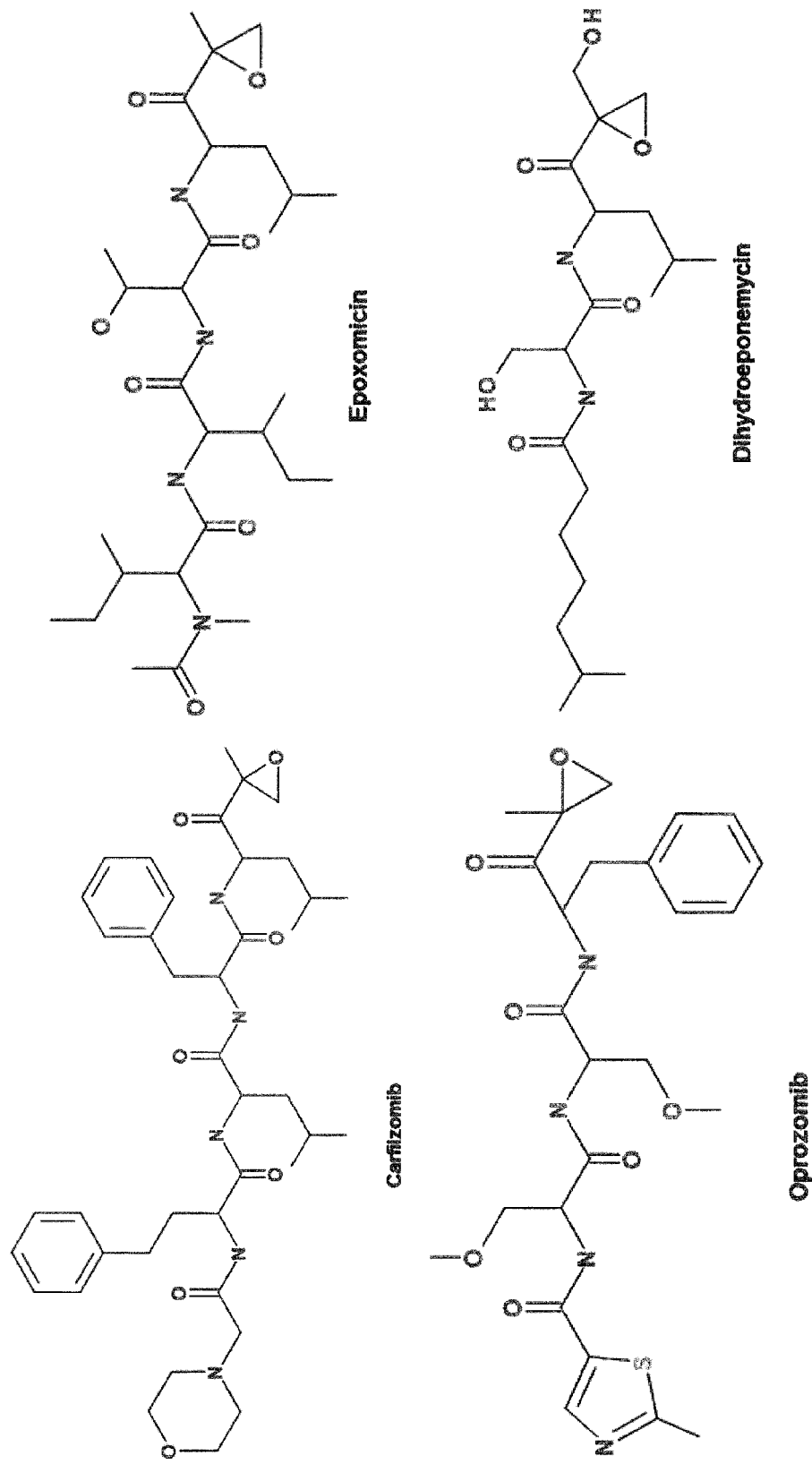

8 Claims, 6 Drawing Sheets
Specification includes a Sequence Listing.

(56) References Cited

OTHER PUBLICATIONS

Gybin et al., "The sequence of a stepwise AdE reaction and intramolecular Pauson-Khand cycloaddition as an entry into the synthesis of polycyclic compounds," J Am Chem, 5555-5566 (1992).
Haken et al., "Gas chromatography of homologous esters," Journal of Chromatography, 324:343-353 (1985).
Harris et al., "Substrate specificity of the human proteasome," Chemistry and Biology, 8(12):1131-1141 (2001).
International Search Report for International Application No. PCT/EP2017/063699 dated Sep. 7, 2017.
Katritzky et al., "Alkyl, unsaturated, (hetero)aryl, and N-protected alpha-amino ketones by acylation of organometallic reagents," The Journal of Organic Chemistry, 71(26):9861-9864 (2006).
Miao et al., "Orthogonal sement ligation," Peptides for the New Millennium, 115-118 (2000).
Nazif et al., "Global analysis of proteasomal substrate specificity using positional-scanning libraries of covalent inhibitors," PNAS, 98(6):2967-2972 (2001).
CA Notice of Reasons for Rejection for Application No. JP 2018-563804 dated Mar. 19, 2021.

\* cited by examiner

Epoxyketone with methyl alcohol substitution

Dihydroeponemycin

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: substrate

<400> SEQUENCE: 1

Leu Leu Val Tyr
1

PROTEASOME INHIBITORS

RELATED APPLICATIONS

This application is a U.S. national-stage filing under 35 U.S.C. 371 of International Application PCT/EP2017/063699, filed Jun. 6, 2017, which claims the benefit of European Application No. 16173057.7, filed Jun. 6, 2016, and U.S. Provisional Application No. 62/346,203, filed Jun. 6, 2016.

SEQUENCE LISTING

The instant application contains a Sequence Listing which has been submitted electronically in ASCII format and is hereby incorporated by reference in its entirety. Said ASCII copy, created on Mar. 12, 2021, is named VPH-01001_SL.txt and is 599 bytes in size.

The present invention relates to a compound of formula (I)

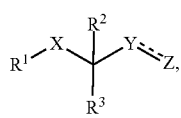

wherein
X is C=O, C=S or B—OH;
Y is an electrophile and Z is a leaving group, or Y=Z is an electrophile;
$R^1$ comprises or consists of
(a) (i) a first group binding to a proteolytic site of a proteasome, said first group being bound to X; and
(ii) optionally a second group enhancing delivery;
or
(b) a group binding between subunits β1 and β2 of a proteasome;
$R^2$ and $R^3$ are independently selected from H, methyl, methoxy, ethyl, ethenyl, ethinyl and cyano, wherein methyl and ethyl may be substituted with OH or halogen.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

In recent years, the proteasome has been validated as a therapeutic target for anti-cancer therapy and the first proteasome inhibitor Bortezomib has been approved in 2008 for the treatment of multiple myeloma and mantle cell lymphoma. Current efforts focus on the development of second generation inhibitors with improved pharmacological properties. Epoxyketone inhibitors of the proteasome are desirable cancer therapeutics. The dose required to elicit inhibition is considerably lower than the boronic acid proteasome inhibitor Bortezomib. Additionally, many patients treated with Bortezomib acquire resistance to this agent through mutations in the β-subunits, i.e. the active site subunits of the proteasome. It has been recognized in recent years that Bortezomib resistant patients are responsive to Carfilzomib, which is the only epoxyketone inhibitor approved for clinical use today. This further highlights the importance of the development of additional epoxyketone inhibitors and/or inhibitors exhibiting similar inhibition properties as epoxyketone inhibitors. In pursuit of this goal most approaches today focus on the modification of the peptide backbone of epoxyketone inhibitors. These modifications include the introduction of natural and non-natural amino acids to increase the specificity for a given proteasome active site, the solubility of epoxyketone inhibitors, the bioavailability and the possibility to orally administer cancer therapeutics. In addition, medicinal chemistry approaches have focused on the addition of capping agents at the S4 position, which increase the absorptive properties of epoxyketone inhibitors and/or protect them from the harshly acidic environment of the gastro-intestinal tract.

The parent molecule of this class epoxyketone proteasome inhibitors, epoxomicin, was first isolated as a natural product synthesized by an *Actinomyces* bacterial strain. Later, another molecule of this class was found, viz. eponemycin, and several synthetic variants of these molecules (FIG. 1) are presently in clinical trials as cancer therapeutics (Bennett and Kirk, Curr. Opin. Drug Discov. Devel., 11, 616-625 (2008); Demo et al., Cancer Res., 67, 6383-6391 (2007)).

The efficacy of epoxyketone inhibitors, is a consequence of the dual electrophile nature of the epoxyketone group. Based on several co-crystal structures of epoxyketone inhibitors with yeast, mouse and human 20S proteasomes, it has been described that the γ-hydroxyl group of the proteasome active site catalytic threonine reacts with the ketone moiety, whereas the N-terminal amino group of Thr1 reacts with the carbon atom of the epoxide of the inhibitor, which is in α-position to the ketone, in an irreversible manner. As shown in Scheme 1, this suggested chemistry results in the formation of an 1,4-morpholine ring product, which is formed by the active site catalytic threonine and the epoxyketone inhibitor (Groll et al., Journal of the American Chemical Society, 122, 1237-1238 (2000)).

Scheme 1: Proposed chemical reaction mechanism for the inhibition of proteasome active sites by epoxy ketone inhibitors (Groll et al., loc. cit.) Initially, the γ-hydroxyl group of the actives site catalytic threonine amino acid side chain esterifies the ketone group of the epoxyketone inhibitor by a nucleophilic attack (left). The nucleophilic addition reaction results in the formation of a hemiketal intermediate where the γ-hydroxyl group of the active site catalytic threonine is reversibly bound to the epoxyketone inhibitor (middle). The N-terminal amino group of the active site catalytic threonine then reacts with the electrophilic carbon atom in α-position to the ketone to form the covalently modified proteasome active site (right). This 1,4-morpholine ring structure which is formed by both the proteasome active site and the inhibitor results in an irreversible inhibition of the proteasome active site.

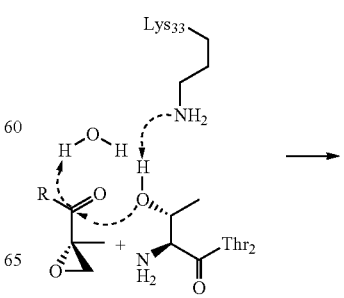

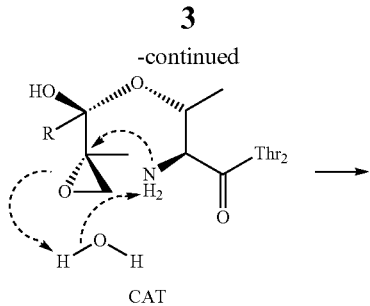

CAT

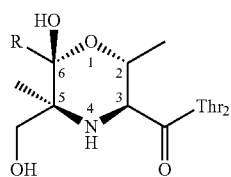

This proposed inhibition scheme was formulated based on crystal structures where the electron density in the 20S proteasome active site was of insufficient resolution and quality to unequivocally model the inhibited state in atomic detail. Yet, the common belief that irreversible proteasome inhibition by epoxyketones yields a six atom ring adduct is well-established in the art; see, for example, the section dedicated to Carfilzomib and references cited therein in the review about proteasome inhibitors by Kubiczkova et al. (J. Cell. Mol. Med., 18, 947-961 (2014)).

There remains a significant need to develop new proteasome inhibitors, in particular improved proteasome inhibitors, improvements including activity at lower dosage and less side effects.

This technical problem has been solved by the subject-matter of the enclosed claims.

Accordingly, the present invention, in a first aspect relates to a compound of formula (I)

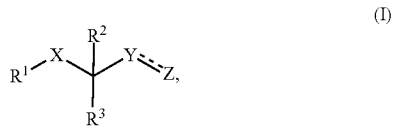

wherein

X is C=O, C=S or B—OH;

Y is an electrophile and Z is a leaving group, or Y=Z is an electrophile;

$R^1$ comprises or consists of (a) (i) a first group binding to a proteolytic site of a proteasome, said first group being bound to X; and (ii) optionally a second group enhancing delivery;

or (b) a group binding between subunits β1 and β2 of a proteasome;

$R^2$ and $R^3$ are independently selected from H, methyl, methoxy, ethyl, ethenyl, ethinyl and cyano, wherein methyl and ethyl may be substituted with OH or halogen.

It is understood that throughout the present specification the term "compound" encompasses pharmaceutically acceptable salts, solvates, polymorphs, prodrugs, codrugs, cocrystals, tautomers, racemates, enantiomers, or diastereomers or mixtures thereof unless mentioned otherwise.

The compounds of formula (I) have a bipartite structure. $R^1$, herein also referred to as "targeting group", is responsible for targeting the compound of formula (I) to the proteolytic site of the proteasome. This part of the compound may build on established knowledge; for details see below. The remainder of said compound is displayed in more detail in formula (I). This part is also referred to as "headgroup" or "warhead" herein. It is responsible for the irreversible inhibition of the proteasome. The headgroup requires an electrophile (Y or Y=Z) in β-position relative to the functional group X. Such a design is contrary to the common belief that irreversible inhibition of the proteolytic site of the proteasome yields a morpholine ring. To explain further, as can be seen in Scheme 1 displayed herein above, the expected mechanism involves a nucleophilic attack of the amino group of Thr1 on a position which is in α to the ketone of the epoxyketone inhibitor. The epoxy group is amenable to such nucleophilic attack, noting that the carbon in α-position to the ketone is electrophile.

The present inventors determined more than 20 crystal structures of the human 20S proteasome at improved resolutions ranging from 1.8-2.2 Å. These new crystal structures of human 20S proteasomes provide insight into the inhibited state at atomic resolution. In contrast to the previously described formation of a 6-membered 1,4-morpholine ring structure for epoxyketone proteasome inhibitors, it is now possible to visualize the formation of a 7-membered 1,4-oxazepane ring structure involving the catalytic threonine residue of the proteasome active site and the inhibitor in the inhibited state. Formation of such an 1,4-oxazepane inhibited state is achieved by a double electrophilic reactive group on the inhibitor, where both electrophiles are in a distance of two atoms to one and another.

This finding allows to propose a novel chemical mechanism for the inhibition of 20S proteasomes by epoxyketone inhibitors. In this reaction mechanism, initially the γ-hydroxyl group of the proteasome active site catalytic threonine reacts with the ketone moiety, similar to the situation where the 1,4-morpholine ring (6-ring) structure is formed. In contrast to established theory, and to allow for 1,4-oxazepane 7-ring formation, the N-terminal amino group of Thr1 reacts in an irreversible manner with that carbon atom of the epoxide of the inhibitor which is in β-position to the ketone (Scheme 2). The reaction with the carbon atom of the epoxide in β-position to the ketone appears to be favored because it is the less substituted center.

Scheme 2: Chemical reaction mechanism for the inhibition of proteasome active sites by epoxyketone inhibitors according to the invention and based on high resolution co-crystal structures with human 20S proteasomes. Initially, the γ-hydroxyl group of the active site catalytic threonine amino acid side chain esterifies the ketone group of the epoxyketone inhibitor by a nucleophilic attack (left). The nucleophilic attack results in the formation of a hemiketal intermediate, where the γ-hydroxyl group of the active site catalytic threonine is reversibly bound to the epoxyketone inhibitor (middle). Until this step, the reaction mechanism for the formerly assumed 1,4-morpholine and the newly evidenced 1,4-oxazepane structures in the inhibited state are identical. For the formation of the 1,4-oxazepane structure, however, the N-terminal amino group of the active site catalytic threonine then reacts with the electrophilic carbon atom of the epoxide in β-position to the ketone to form the covalently modified proteasome active site (right). This 1,4-oxazepane ring structure, which is formed by both the proteasome active site and the inhibitor results in an irreversible inhibition of the proteasome active site.

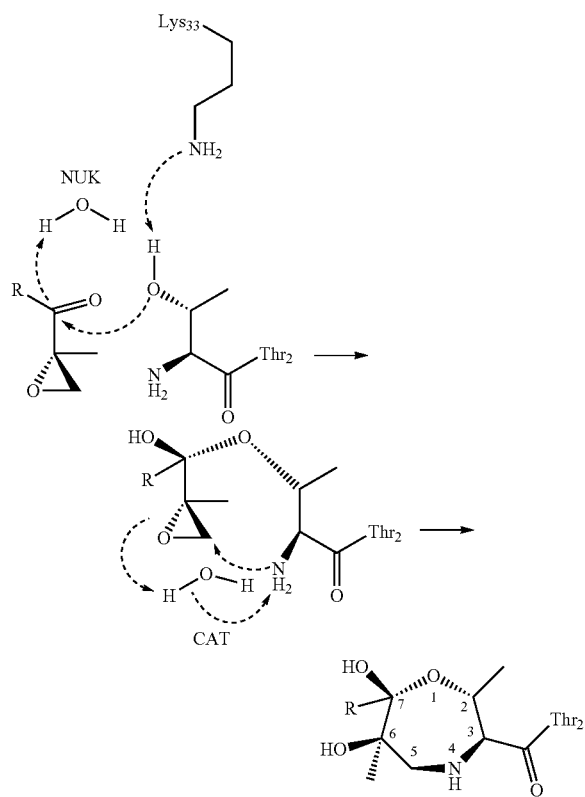

From a theoretical perspective, epoxyketone inhibitors are capable of forming either type of adduct, namely a 6-ring or a 7-ring. However, the formation of a 7-ring adduct has never been considered. Instead, the prior art is consistent in that a morpholine ring would be formed. The present inventors' work is first to establish that a 7-ring adduct is formed. As a consequence, the present inventors are the first to disclose the specific molecular architecture as laid down in formula (I) which is specifically tailored for the formation of a 7-ring adduct. The inhibitory activity of the art-established epoxyketones entirely fails to suggest this mechanism. Only in view of the high resolution crystal structures, the present inventors were able to discover the β-regiospecificity of the nucleophilic attack of the active site threonine residue of the proteasome.

Without wishing to be bound to a specific theory, the present inventors furthermore consider that the formation of a seven ring adduct is kinetically favoured. Therefore, the provision of the compounds of the first aspect of the present invention which are specifically tailored for said kinetically favoured reaction mechanism will allow the use of lower dosages. As a consequence, fewer side effects are expected.

X is a functional group providing an electrophile. It can be a keto group, a thio-keto group or a boronic acid group. Deviant from the boronic acid group as present, for example, in Bortezomib, the compound of formula (I) requires that boron is part of the main chain. As shown in Scheme 2, the oxygen of the hydroxy group of the active site threonine residue of the proteasome binds to the electrophile atom in group X (the carbon atom or the boron atom).

The group Y—Z defines a second electrophile. Either Y as such or Y—Z as a whole is electrophile; for preferred implementations see further below.

Moieties $R^2$ and $R^3$ define the intervening portion of the compound between the two electrophiles.

$R^1$ is the above mentioned targeting moiety. Targeting moieties are known in the art. In many instances, targeting moieties are peptidic in nature. This applies, for example, to Epoxomicin, Oprozomib, Carfilzomib, Dihydroeponomycin, Eponemycin and ONX-0914. Since the active site of the proteasome exhibits proteolytic activity, peptides generally bind to said active site and are accordingly useful for targeting.

Said first group may optionally be bound to a second group which second group enhances delivery. To the extent the first group is peptidic in nature and consists of three amino acids or derivatives thereof, said second group may occupy a fourth position, in the art also referred to as S4 position. Dorsey et al. (J. Med. Chem., 51, 1068-1072 (2008)) and Zhou et al. (J. Med. Chem., 52, 3028-3038 (2009)) explored several suitable groups which are attached to the N-terminal end of a peptidic first group. These groups attached to the N-terminal end of a peptidic first group as described in these two publications all constitute suitable second groups in accordance with the present invention.

An alternative term for said second group is "N-cap".

While peptidic first groups are envisaged, the particular structure of the targeting group is not key to the present invention. Basically, any chemical group which provides for targeting to a proteolytic site in the proteasome or to the vicinity thereof is a suitable group $R^1$ in accordance with the present invention. To the extent a targeting group does not target directly to the proteolytic site, but to another site of the proteasome in the vicinity of the proteolytic site, linkers of suitable length may be used to connect the targeting group $R^1$ to the active element of the compound of the first aspect, said active element comprising groups X, Y and Z.

To give an example of alternative targeting groups, Beck et al. (Angew. Chem. Int. Ed. 54, 11275-11278 (2015)) describe a molecule binding to the crevice between β1 and β2 subunit of the proteasome. This compound is displayed below.

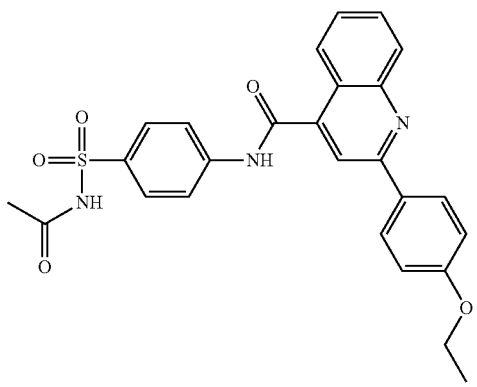 [SMILES: CCOc1ccc(-c2cc(C(=O)Nc3ccc(S(=O)(=O)NC(C)=O)cc3)c3ccccc3n2)cc1]

Replacing the ethyl group of the ethoxy moiety bound to the phenyl group of said compound is a means of rendering this molecule suitable group $R^1$. This is explained in further detail below.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups.

To the extent compounds of the invention exhibit a pH-dependent charged state, it is understood that all possible charged states are embraced. A preferred pH range in this regard is from 0 to 14.

To the extent a compound according to the invention bears a net charge, it is understood that the compound is provided in electroneutral form. This is achieved by one or more counterions, preferred counterions being defined in relation to the term "salt" herein above.

In a preferred embodiment, said first group is a peptidic group comprising or consisting of at least two amino acids, or a corresponding peptidomimetic, wherein X takes the place of the carbonyl group or of the α-carbon of the C-terminal amino acid of said peptidic group, and said second group, if present, is bound to the N-terminus of said peptidic group.

Preferred amino acids are α-amino acids. Preferred α-amino acids are the 20 proteinogenic amino acids. Also preferred are derivatives of said proteinogenic amino acids, for example, the methyl ester of serine, also denoted "Ser (OMe)". Other derivatives of the proteinogenic amino acids may be used as well, for example those described in Zhou et al. loc. cit. and including 4-diazolyl-alanine, homoserine methyl ester, pyridyl alanines such as 2-pyridyl alanine, 3-pyridyl alanine and 4-pyridyl alanine; 3-thienyl alanine, cyclohexyl alanine, cyano alanine and methyl serine.

Also other α-amino acids such as 2-amino butyric acid may be used.

In further preferred embodiments, β-amino acids may be used in one or more positions of the peptidic group. Also preferred is to use D-amino acids at one or more positions.

As an alternative to peptide bonds, alternative functional groups may be used. This may apply to a single peptide bond or to two or more peptide bonds. If all peptide bonds are replaced by other functional groups, the backbone chemistry in its entirety is changed. Alternative backbones are known in the art and include polyactide (PLA), alkylamines, jeffamines and those shown below ((a) to (r)) and described in Grimm et al. (Acta Cryst D (2010), 66, 685-697).

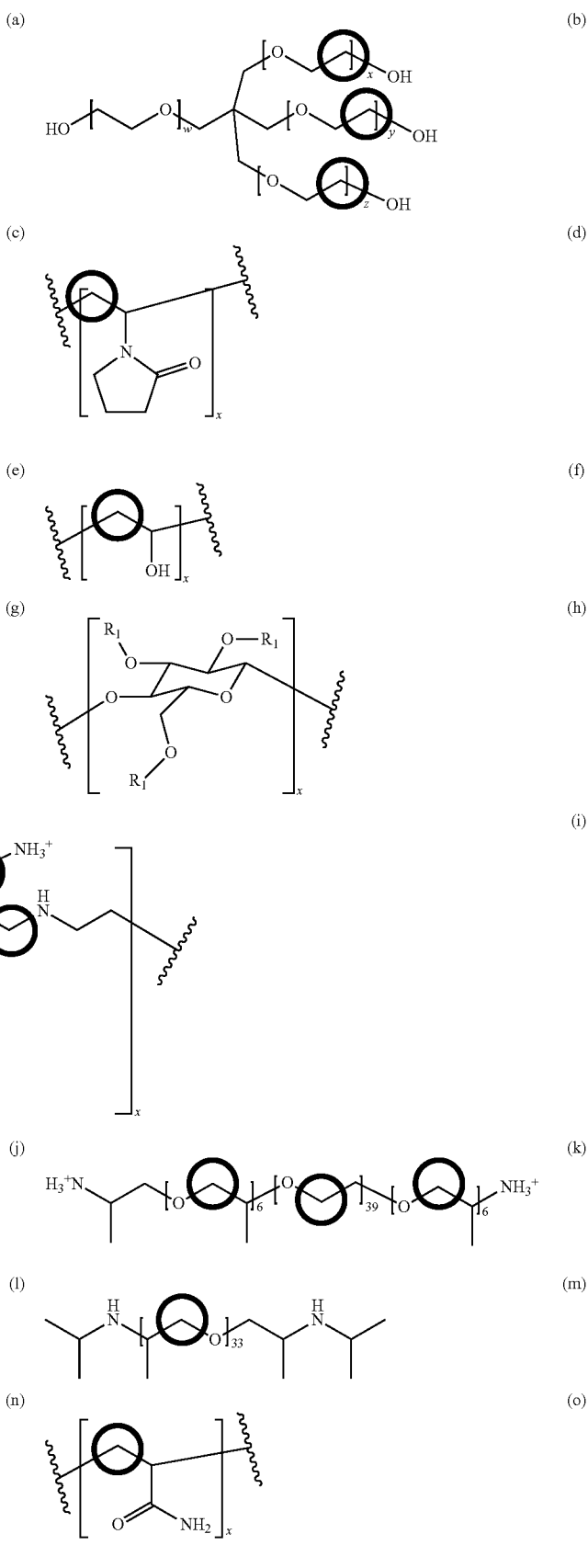

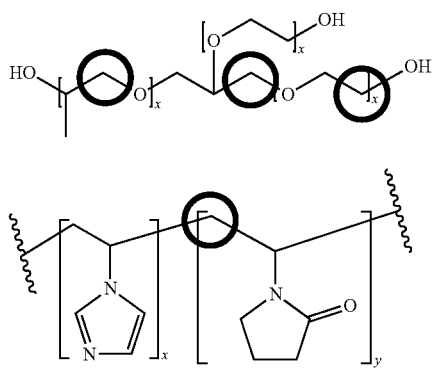
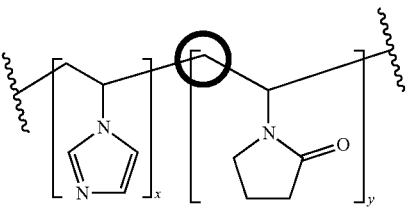

The above displayed backbones are as follows.

(a) M-type Jeffamines. $R_1$=—H for ethylene oxide (EO) or —$CH_3$ for propylene oxide (PO). The PO/EO molar ratio is 29/6 for Jeffamine M2005, 10/31 for Jeffamine M2070 and 9/1 for Jeffamine M600. (b) Pentaerythritol ethoxylate. (c) Pentaerythritol propoxylate. (d) Polyvinyl pyrrolidone. (e) Polypropylene glycol. (f) Polyvinyl alcohol. (g) Polyacrylate. (h) Cellulose-based polymers. $R_1$=—H, —$CH_3$ or —$CH_2CHOHCH_3$ (hydroxypropyl methylcellulose), —H or $CH_2CO_2H$ (carboxymethyl cellulose). (i) Poly(ethylene imine). (j) Di[poly(ethyleneglycol)]adipate. (k) Jeffamine ED2003. (l) Jeffamine D2000. (m) Jeffamine SD2001. (n) T-type Jeffamines. (o) Polyacryl amide. (p) Glycerol ethoxylate. (q) Acrylic acid/maleic acid copolymer. (r) Vinylpyrrolidone/vinylimidazole copolymer. Each of the indices x, y, z and w is independently chosen from the integer numbers 0, 1, 2, 3, 4, 5, 6, 7, 8, 9 and 10, provided that a minimal length of at least two, preferably three building blocks is obtained. While branched backbones such as those depicted in (b) and (c) are not excluded, preference is given to backbones which are not branched. Accordingly, in the formulae for branched backbones such as (b) and (c), preference is given to two indices selected from x, y and z being 0. Potential positions for amino acid side chains are denoted as ellipses in the figure. These positions correspond to the $C^\alpha$ atmons in a peptide.

More generally speaking, the peptidic group may be replaced by a corresponding peptidomimetic. The term "corresponding" in this context means that the peptidomimetic has similar size when compared to a peptidic group. Accordingly, a peptidic group consisting of two amino acids and a peptidic group consisting of three amino acids, respectively, each impose size limits on a corresponding peptidomimetic. A peptidomimetic in accordance with the present invention may use the above mentioned alternative backbones and/or any of the mentioned non-proteinogenic amino acids, noting that amino group and/or carboxylic group of any non-proteinogenic amino acid may be further modified in order to account for the mentioned alternative backbone.

In terms of secondary structure, preference is given to peptidic groups, corresponding peptidomimetics or backbones which are capable of assuming a β-sheet structure. Specific backbones capable of assuming a β-sheet structure include peptide bonds and the alternatives described above.

As disclosed above, X may take the place of the carbonyl group of the α carbon of the C-terminal amino acid of said peptidic group. In other words, and assuming that X is CO which is preferred, X is the carbonyl group of said C-terminal amino acid. In the alternative, the α-carbon may be replaced with X. In that case, the C-terminal amino acid of said peptidic group may be viewed as a truncated amino acid. Having said that, it is formally considered as a separate building block and is also referred to as S1 site of the proteasome inhibitor.

The term "peptidic" refers to peptide bonds connecting the amino acids of said group. The C-terminal end of the peptidic group is the end which is connected to X. To the extent the peptide bonds are inverted, i.e. NHCO instead of CONH, this is a preferred embodiment falling under the term "peptidomimetic".

Detailed exemplary synthesis procedures for two preferred compounds are given in the examples. In the following, general synthesis procedures are disclosed.

Synthesis of active ester: A) Beta-Keto acid formation from Boc-L-amino acid, esterification for the protection of beta-carboxyl moiety. B) Methylation reaction. C) Boc-Deprotection. D) Peptide coupling. E) Saponification of ester to Beta-Keto acid (partially instable). F) Preparation of an active ester with N-Hydroxysuccinimide.

Synthesis of a Beta-Ketoaldehyde: G) Preparation of a Weinreb-Amide from Boc-L-amino acid. H) Gringard reaction to obtain alpha-Dioxacyclopentyl Ketone. Methylation Reaction. I) Boc-Deprotection. J) Peptide coupling. K) Oxidation to Beta-Ketoaldehyde.

Tripeptide Synthesis: L) Protection of the carboxyl group of Boc-L-Amino Acid by esterification. M) Boc-Deprotection. N) Peptide coupling with Boc-L-amino acid. O) Boc-Deprotection. P) Coupling with N-cap acid. Q) Saponification of ester to acid.

As an alternative to $R^1$ being a peptidic group or a peptidomimetic, a group binding between subunits β1 and β2 of the proteasome may be used. Preferably, said group is an aryl sulfonamide, aryl preferably being phenyl, aryl being connected to $R^{12}$ as defined in the following. Between said aryl sulfonamide and $R^{12}$ further moieties may be present, said further moieties preferably being isosteric with the corresponding moieties of the particularly preferred group binding between subunits β1 and β2 as disclosed in the following. Particularly preferred is that said group binding between subunits β1 and β2 is 4-[2-(4-$R^{12}$-oxy-phenyl) quinolin-4-yl carboxamido] benzene N-acetyl sulfonamide. $R^{12}$ is a linker connecting said group binding between subunits β1 and β2 to X, preferably being $C_5$ to $C_{10}$ alkyl, $C_5$ to $C_{10}$ alkenyl or —[O—$(CH_2)_2]_{1-5}$, wherein one or more C atoms in said linker may be replaced with O and/or N.

Said alkenyl group may comprise one, two or more double bonds.

So far, the group Y=Z has been displayed as a double bond, wherein one of the two bonds comprised in the double bond is dashed. This indicates that Y and Z may either be connected by a double bond or a single bond.

In a preferred embodiment, Y=Z is Y=Z, and preferably selected from CH=O or CH=CH$_2$. In an alternative, Y=Z is Y—Z and is preferably selected from CH$_2$—I, CH$_2$—Br, CH$_2$—Cl, CH$_2$—OPO(OH)$_2$, CH$_2$—OTs or CO—NHS wherein OTs is p-toluene sulfonyloxy and NHS is N-oxy-succinimide. As an alternative to the NHS-activated ester, also other activated esters known in the art may be used.

In a further alternative preferred embodiment, Y=Z is Y—Z and preferably selected from O—I, O—Br, O—Cl, S—I, S—Br and S—I.

In a further preferred embodiment, $R^2$ and $R^3$ are identical and preferably methyl, H, methoxy or —CH$_2$OH. Particularly preferred is that both $R^2$ and $R^3$ are methyl or that both $R^2$ and $R^3$ are H. Especially preferred is that both $R^2$ and $R^3$ are methyl.

Preferred is that X is CO.

Preferred is that Y=Z is CH=O. Also preferred is that Y=Z is CO—NHS.

Particularly preferred is that X is C=O and Y—Z is CH=O or CO—NHS.

Particularly preferred is that X is C=O and Y—Z is CH=O or CO—NHS and both $R^2$ and $R^3$ are methyl.

The following preferred embodiments are dedicated to preferred implementations of the targeting moiety $R^1$. Any of the preferred embodiments of $R^1$ can be combined with any of the preferred embodiments of X, Y, Z, $R^2$ and $R^3$.

In a preferred embodiment, said peptidic group consists of three α-amino acids, wherein preferably (a) the N-terminal amino acid is selected from Ser(OMe), Leu, Phe and Ala; the middle amino acid is selected from Ser(OMe), Leu, Phe and Ala; and/or the C-terminal amino acid is selected from Phe, Tyr, Leu, Ser(OMe) and Ala; or (b) said peptidic group consists of Ser(OMe)-Ser(OMe)-Phe, Leu-Leu-Tyr or Ala-Ala-Ala.

Said N-terminal amino acid is also referred to as the moiety defining the S3 site of the inhibitor. Said middle amino acid defines the S2 site. Said C-terminal amino acid defines the S1 site.

In a further preferred embodiment, said group enhancing delivery is present and is $R^{11}$—CO, $R^{11}$—CS—, or $R^{11}$—SO$_2$—,
$R^{11}$ being selected from the following substituted or unsubstituted groups, groups being carbocyclyl, heterocarbocyclyl, carbocyclyl alkyl, heterocarbocyclyl alkyl, alkyl heterocarbocyclyl alkoxy heterocarbocyclyl, alkoxyalkyl heterocarbocyclyl, heterocarbocyclyl amino, heterocarbocyclyl alkyl heterocarbocyclyl, and alkyl heterocarbocyclyl alkyl heterocarbocyclyl,
wherein alkyl is $C_1$ to $C_4$ alkyl, preferably methyl, substituents are $C_1$ to $C_4$ alkyl, preferably methyl or ethyl, $C_1$ to $C_4$ alkoxy, preferably methoxy or ethoxy, hydroxy and/or halogen, preferably Cl, Br or I, and heteroatoms are O, N and/or S.

$R^{11}$—CO is particularly preferred.

$R^{11}$ being heterocarbocyclyl is particularly preferred.

The term "carbocyclyl" designates a ring molecule, wherein the ring comprises carbon atoms.

The ring may be formed exclusively by carbon atoms, but does not have to. Accordingly, one, two or more heteroatoms may be present. The ring may be saturated in which case it would be a cyclic alkane, optionally comprising one or more heteroatoms. The ring may contain one, two or more double bonds. If said double bonds are conjugated, carbocyclyl is an aryl moiety.

In a particularly preferred embodiment, (a) said carbocyclyl is aryl or biaryl, aryl being monocyclic or bicyclic and preferably phenyl or naphthyl; and (b) said heterocarbocyclyl is heteroaryl, heteroaryl being monocyclic or bicyclic, bi-heteroaryl, aryl heteroaryl, heteroaryl aryl or heterocycloalkyl, heteroaryl preferably being furyl, thienyl, oxazolyl, isoxazolyl, pyrazolyl, imidazolyl, thiazolyl, pyridinyl, pyrazinyl, pyridazinyl or quinolinyl, aryl preferably being phenyl, heterocycloalkyl preferably being morpholinyl or tetrahydrofuranyl.

Particularly preferred is that heterocarbocyclyl is heteroaryl, in particular monocyclic heteroaryl.

In a particularly preferred embodiment $R^{11}$ is selected from 2-methyl thiazol-5-yl; 4-morpholinyl methyl; 1,4-dichloro 2-phenyl; 6-phenylpyridin-2-yl; pyrazin-2-yl; 3-furyl; 2-thienyl; 5-oxazolyl; 5-isoxazolyl; (5-Me)-3-isoxazolyl; (5-iPr)-3-isoxazolyl; (5-MeOCH$_2$)-3-isoxazolyl; 3-pyrazolyl; 2-imidazolyl; (N-Me)-3-pyrazolyl; (N-Me)-2-imidazolyl; (5-Me)-3-pyrazolyl; 4-pyridinyl; 4-pyridazinyl; 2-(R)-tetrahydrofuranyl; 2-(S)-tetrahydrofuranyl; (5-Me)-3-isoxazolyl-NH—; pyrazin-2-yl; naphth-2-yl; quinolin-2-yl; 4-biphenyl; 3-biphenyl; 4-phenylpyridin-2-yl; 3-phenyl-pyridin-2-yl; 5-phenylpyrazin-2-yl; 6-phenylpyrazin-2-yl; 2-phenyl-thiazol-4-yl; and 5-$R^{111}$-isoxazol-3-yl;
wherein $R^{111}$ is selected from methyl, 4-morpholinyl methyl, 1,2,4-triazolyl methyl, imidazolyl methyl and N-methyl piperazinyl methyl.

Especially preferred is that $R^{11}$ is 2-methyl thiazol-5-yl.

Especially preferred compounds of the first aspect are the compounds of formulae (IIa) and (IIb):

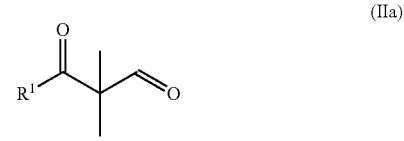

(IIa)

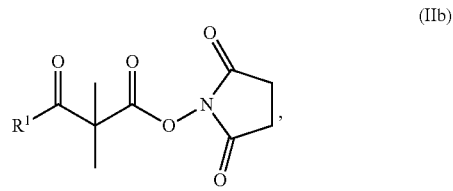

(IIb)

wherein $R^1$ is $R^{11}$—CO-Ser(OMe)-Ser(OMe)-NH—CH (CH$_2$—C$_6$H$_5$), $R^{11}$ being as defined above, and wherein most preferably $R^1$ is 2-methyl thiazol-5-yl carbonyl Ser (OMe)-Ser(OMe)-NH—CH(CH$_2$-C$_6$H$_5$).

In a second aspect, the present invention provides the use of a compound as defined in the first aspect as a proteasome inhibitor.

One or a plurality of compounds in accordance with the first aspect may be used.

Preferably, said proteasome is a proteasome core particle (CP) which is also known as 20S proteasome. In a preferred embodiment, the constitutive core particle (cCP) is used. Alternatively, tissue-specific proteasomal subtypes such as immunoproteasome (iCP) or the thymusproteasome (tCP) may be used.

A proteasome inhibitor in accordance with the present invention is a compound which inhibits one or more proteolytic activities of a proteasome. A proteasome comprises a plurality of proteolytic sites. Preferably, said proteolytic sites are as follows: a site with caspase-like proteolytic activity, a site with trypsin-like proteolytic activity and a site with chymotrypsin-like proteolytic activity. Proteasome inhibitors in accordance with the present invention are capable of inhibiting at least one of these sites. Preferred are compounds which are capable of inhibiting two or all three of these sites.

Related thereto, the present invention provides, in a third aspect, a method of inhibiting a proteasome, said method comprising bringing into contact a proteasome and a compound as defined in the first aspect, provided that methods for treatment of the human or animal body by therapy and diagnostic methods practised on the human or animal body are excluded and/or said method is performed in vitro or ex vivo.

Also provided is a method of inhibiting a proteasome, said method comprising bringing into contact a proteasome and a compound as defined in the first aspect. The method may be performed in vivo.

It is understood that said bringing into contact is effected under conditions which allow a physical contact between said compound and the proteasome. Suitable conditions include aqueous solutions, such as buffered aqueous solutions. Exemplary conditions can be found in the examples enclosed herewith.

The examples include also a proteasome activity assays in accordance with the invention.

A preferred proteasome activity assay is as follows. The activity assay is based on the cleavage of 7-amino-4-methyl-coumarin (AMC) substrates consisting of the fluorophore AMC fused N-terminal to a peptide backbone. These substrates are fluorogenic as the cleaved AMC exhibits fluorescence (emission wavelength: 380 nm; emission wavelength: 460 nm). For every active site a specific substrate is used (LLVY-AMC (SEQ ID NO: 1) for the chymotryptic-like site, LLE-AMC for the caspase-like site, and RLR-AMC for the tryptic-like site). Proteasome activity is monitored by first mixing inhibitor and substrate simultaneously in assay buffer and incubation for 3 min at 37° C. After the addition of 50 nM proteasome and mixing, the increase in fluorescence (excitation wavelength: 380 nm; emission wavelength: 460 nm) is monitored with a spectrofluorimeter. DMSO concentration is kept≤2% for all measurements. The fluorescence readout correlates with proteasome activity. This procedure is utilized to determine the first-order rate constant of inhibition. The $IC_{50}$, which refers to the inhibitor concentration needed to decrease enzyme activity by 50%, can be determined by measuring proteasome activity at varying inhibitor concentrations.

In a fourth aspect, the present invention provides a medicament or lead compound for developing a medicament comprising or consisting of a compound as defined in the first aspect.

The terms "medicament" and "pharmaceutical composition" are used equivalently herein. A pharmaceutical composition in accordance with the present invention may comprise a pharmaceutically acceptable carrier, diluent or excipient.

Examples of suitable pharmaceutically acceptable carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection. The compositions may also be administered directly to the target site, e.g., by biolistic delivery to an external or internal target site. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 µg to 10 mg units per kilogram of body weight per minute. Preferred doses are in the range from about 10 to about 40 $mg/m^2$ body surface, which correspond to about 0.25 to about 1 mg/kg body weight.

One or more compounds in accordance with the first aspect of the present invention may be the only pharmaceutically active agent(s) comprised in a medicament in accordance with the present invention. Alternatively, one, two or more further pharmaceutically active agents may be present. Said further pharmaceutically active agents are preferably selected from known proteasome inhibitors and/or therapeutic agents for the treatment of multiple myeloma. Known proteasome inhibitors are discussed above and include bortezomib, carfilzomib, ixazomib, marizomib, oprozomib, delanzomib, epoxomicin, dihydroeponemycin. Exemplary agents for the treatment of multiple myeloma are lenalidomide and dexamethasone as well as the combination of the latter two.

The development of a lead compound into a medicament is also known as lead optimization.

Methods for the optimization of the pharmacological properties of lead compounds are known in the art and comprise a method of modifying a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physico-chemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carboxylic acids, or (iii) esterification of hydroxyl groups to, e.g. phosphates, pyrophosphates or sulfates or hemi-succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiazolidines or combinations thereof.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

In a fifth aspect, the present invention provides a compound as defined in the first aspect for use in a method of treating, ameliorating or preventing cancer, an autoimmune disease, muscular dystrophy, emphysema, or cachexia accompanying cancer or AIDS.

More generally speaking, the compounds in accordance with the invention are useful in methods of treating, ameliorating or preventing any condition which is amenable to treatment, prevention or amelioration via inhibition of a proteasome.

In a preferred embodiment, said cancer is a lymphoid malignancy, preferably selected from multiple myeloma (MM) including relapsed and refractory MM; non-Hodgkin lymphoma such as B-cell lymphomas including mantle cell lymphoma (MCL) and diffuse large B-cell lymphoma (DLBCL), and Waldenström macroglobulinaemia.

In a further preferred embodiment said autoimmune disease is rheumatoid arthritis, systemic lupus erythematosus, Sjörgen's syndrome or scleroderma.

In a sixth aspect, the present invention provides a method of identifying a compound capable of inhibiting a proteasome, said method comprising bringing into contact a test compound of formula (III)

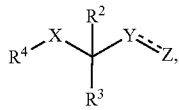

(III)

wherein $R^4$ is an organic group, and X, Y, Z, $R^2$ and $R^3$ are as defined in accordance with the first aspect or preferred embodiments thereof,
with a proteasome, wherein a decreased activity of the proteasome in presence of said test compound as compared to the absence thereof is indicative of said test compound being a compound capable of inhibiting a proteasome.

This aspect relates to a screening method. Screening may be a biochemical screen or a cellular screen. Generally speaking, a variety of assay designs are available for the purpose of identifying compounds which are capable of inhibiting the activity of a given target molecule, here a proteasome. One of the established distinctions is between cellular assays and biochemical assays. Cellular assays are sometimes viewed as mimicking closer the in vivo situation, however, they suffer from the drawback that any candidate compound generally has to pass the cell membrane in a first step. Biochemical assays are simpler in that respect. The target, here a proteasome, may be presented in enriched or purified form in aqueous solution. In such an assay scenario there is no membrane barrier. The conditions, though, may be further remote from the environment in the organism to be subjected to therapy.

A negative control for the screen is the absence of any test compound as disclosed above. As positive controls one or more compounds in accordance with the first aspect or known proteasome inhibitors as disclosed herein may be used.

As known in the art, screening methods may be implemented in a high throughput fashion.

Accordingly, said method may be effect in a high throughput format. High throughput assays generally may be performed in wells of microtiter plates, wherein each plate may contain 96, 384 or 1,536 wells. Handling of the plates, including incubation at temperatures other than ambient temperature, and bringing into contact of these compounds with the assay mixture is preferably effected by one or more computer controlled robotic systems including pipetting devices. In case large libraries of test compounds are to be screened and/or screening is to be effected within short time, mixture of, for example 10, 20, 30, 40, 50 or 100 test compounds may be added to each well. In case a well exhibits biological activity, in the present case inhibition of a proteasome, said mixture of test compounds may be de-convoluted to identify one or more test compounds in said mixture giving rise to said activity.

A compound capable of inhibiting a proteasome is also referred to as proteasome inhibitor.

Inhibition preferably amounts a decrease of activity of at least 10%, at least 20%, at least 30%, at least 40%, at least 50%, at least 60%, at least 70%, at least 80% or at least 90%. Further preferred is a $10^2$-fold, $10^3$-fold, $10^4$-fold, $10^5$-fold, $10^6$-fold, $10^7$-fold, $10^8$-fold or $10^9$-fold reduction of activity.

An art-established measure of inhibitory activity is the $IC_{50}$ value which is the inhibitor concentration where 50% inhibition occurs. Preferably, proteasome inhibitors to be identified by the method of identifying of the present invention as well as compounds in accordance with the first aspect exhibit $IC_{50}$ values in the one digit μM range, preferably below 1 μM, more preferably below 100 nM, below 10 nM, below 1 nM, or below 100 μM. $IC_{50}$ values are preferably determined using the proteasome activity assay as described above.

In accordance with the method of the sixth aspect, $R^4$ is not particularly limited. In fact, one of the applications of this method is the identification of further targeting moieties which targeting moieties may be different from the targeting moieties defined in relation to the first aspect of the invention.

As noted above, $R^4$ is an organic group. It may have a molecular weight between 200 and 1,000 Da.

In a preferred embodiment, said activity is a proteolytic activity, preferably selected from caspase-like, trypsin-like and chymotrypsin-like activity.

In a further preferred embodiment said proteasome is comprised in an in vitro or ex vivo cell.

This preferred embodiment refers to a cellular assay.

A preferred cellular assay is as follows. Cells (e.g. HEK 293) are transfected with the pZsProSensor-1 vector (Clontech Laboratories, Inc.), a reporter gene construct for proteasomal activity. This vector encodes for a destabilized green fluorescent protein variant (ZsGreen) fused C-terminally to a specific degradation motif mediating the recognition and degradation by the proteasome. The fluorescence readout (excitation wavelength: 493 nm; emission wavelength: 505 nm) of expressed ZsGreen is used to monitor proteasome activity. Inhibition of the proteasome causes accumulation of ZsGreen correlating with an increased fluorescence signal in the GFP channel.

In a seventh aspect, the present invention provides a compound of formula (IV)

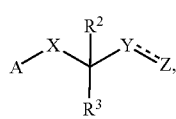

(IV)

wherein
A is selected from NH—NH$_2$, N$_3$ and a click chemistry functional group;
X, Y, Z, R$^2$ and R$^3$ are as defined above.

In an eighth aspect, the present invention provides the use of a compound of formula (IV)

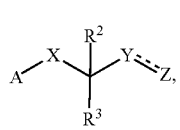

(IV)

wherein
A is selected from NH—NH$_2$, N$_3$ and a click chemistry functional group;
X, Y, Z, R$^2$ and R$^3$ are as defined above;
in the synthesis of a proteasome inhibitor, of a pharmaceutically active agent or of a lead compound for the development of a pharmaceutically active agent, said pharmaceutically active agent preferably being for use in a method of treating or preventing cancer or an autoimmune disease.

The latter two aspects of the invention are directed to the headgroup or warhead of proteasome inhibitors in accordance with the present invention.

Generally speaking, A is a reactive group. Art-established reactive groups may be used. The purpose of A is to provide robust irreversible coupling to targeting moieties such as R$^1$ as defined above. The reactive group A may be used for coupling to any targeting moiety. Upon coupling to a targeting moiety, compounds in accordance with the first aspect may be obtained.

"Click-chemistry is an art-established term; see e.g. Kolb et al. (2001) Click chemistry: diverse chemical function from a few good reactions. Angew. Chem. Int. Ed. 40 (11):2004; Sletten et al. (2009) Bioorthogonal Chemistry: Fishing for Selectivity in a Sea of Functionality. Angew. Chem. Int. Ed. 48:6998; Jewett et al. (2010) Cu-free click cycloaddition reactions in chemical biology. Chem. Soc. Rev. 39(4):1272; Best et al. (2009) Click Chemistry and Bioorthogonal Reactions: Unprecedented Selectivity in the Labeling of Biological Molecules. Biochemistry. 48:6571; and Lallana et al. (2011) Reliable and Efficient Procedures for the Conjugation of Biomolecules through Huisgen Azide-Alkyne Cycloadditions. Angew. Chem. Int. Ed. 50:8794.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1: Chemical structures of representative members of the epoxyketone class of proteasome inhibitors. Shown are the natural products epoxomicin (top right) and dihydroeponemycin (bottom right), which were isolated from bacterial strains. Also depicted are synthetic derivative of the parent natural product molecules. Carfilzomib (top left) was recently approved for the treatment of multiple myeloma and is currently in clinical trials for the treatment of other cancers. Oprozomib is currently in clinical trials as an orally available multi-potent inhibitor for the treatment of several cancers.

Figure 2:
Figure 2:
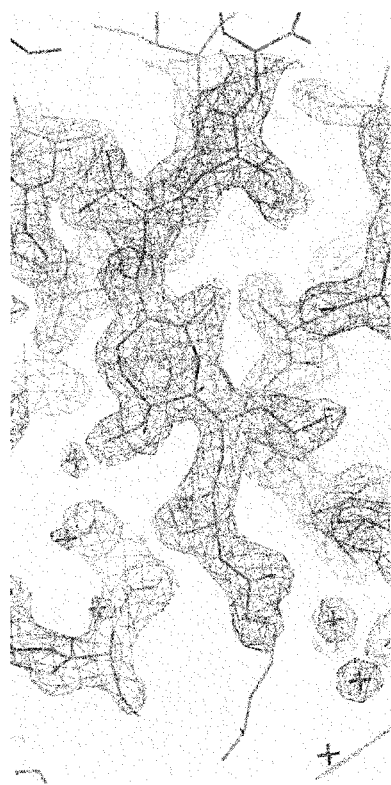
Figure 2:
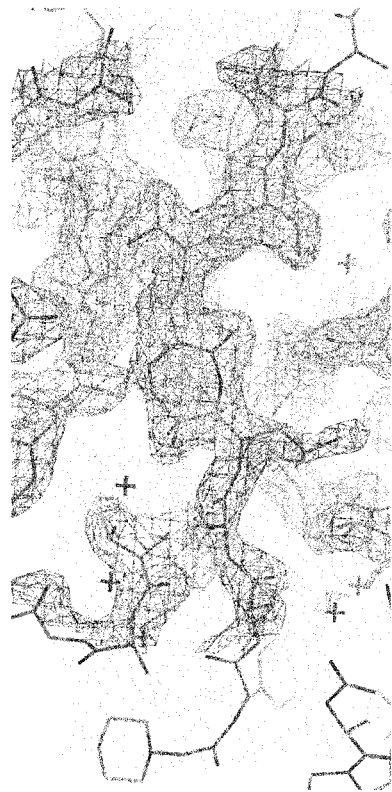
Figure 2:
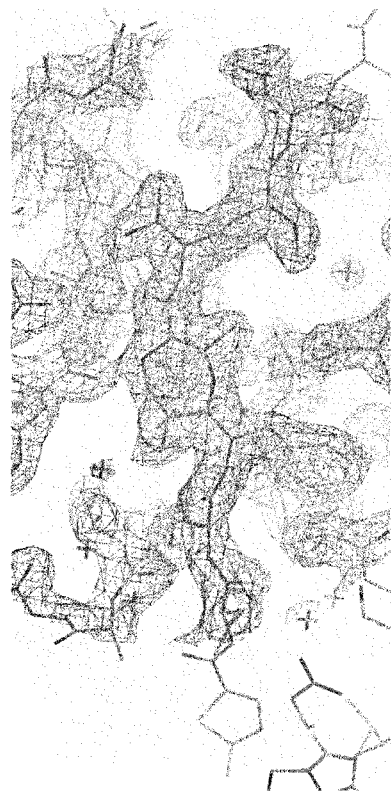

FIG. 2: Crystal structures of co-crystal structures of human 20S proteasomes in complex with epoxyketone inhibitors. 2Fo-Fc electron density maps are shown contoured at 1.5σ for the proteasome active site inhibited with carfilzomib (top left), oprozomib (bottom left), epoxomicin (top right) and dihydroeponemycin (bottom right). Note that the electron density map reveals density for an additional carbon atom. In all cases, the modeled cyclic ring structure is consistent with a 1,4-oxazepane structure formed by the reaction of epoxyketone inhibitors with the active site catalytic threonine side chain.

Figure 3:
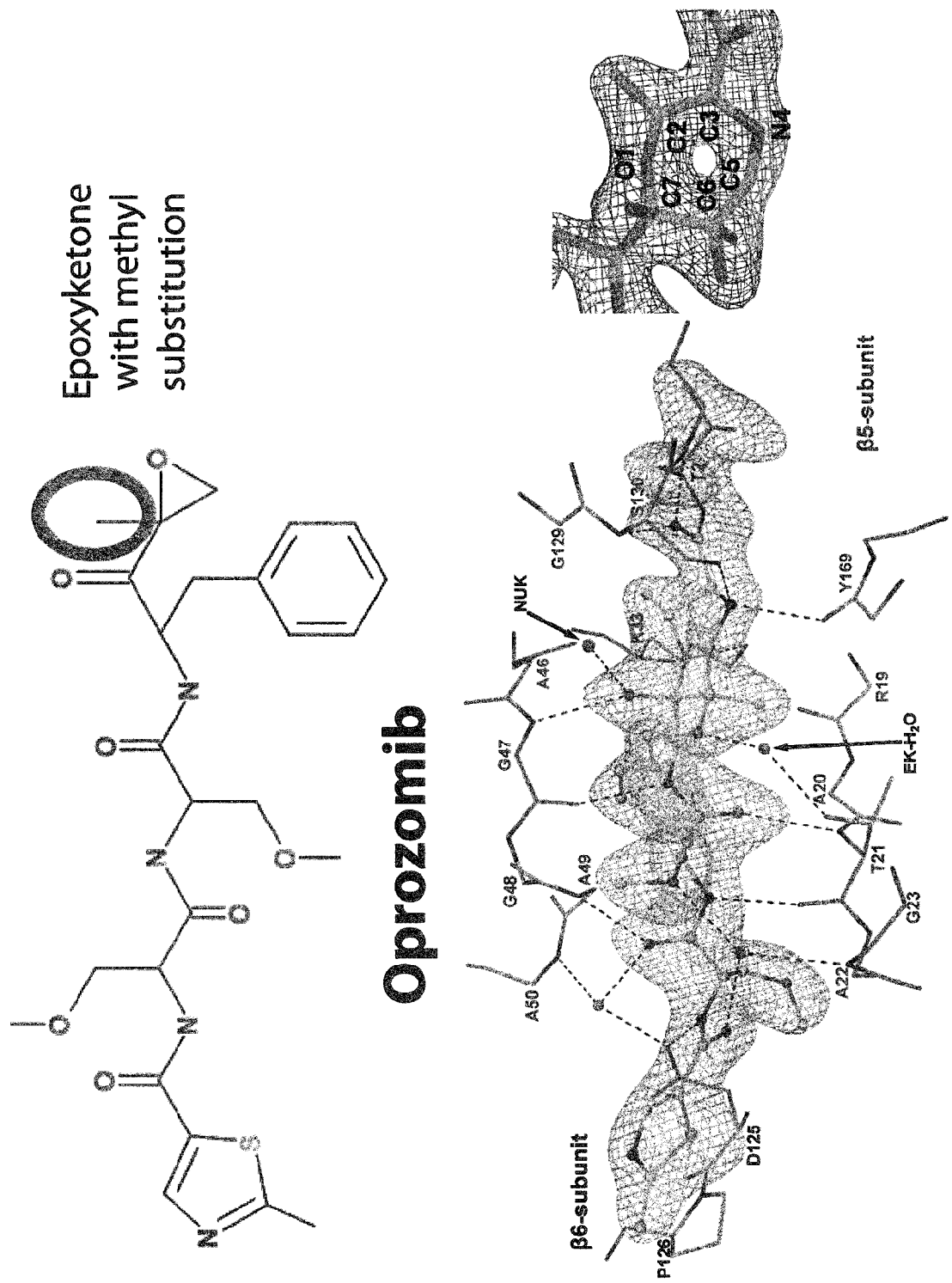
Figure 3:
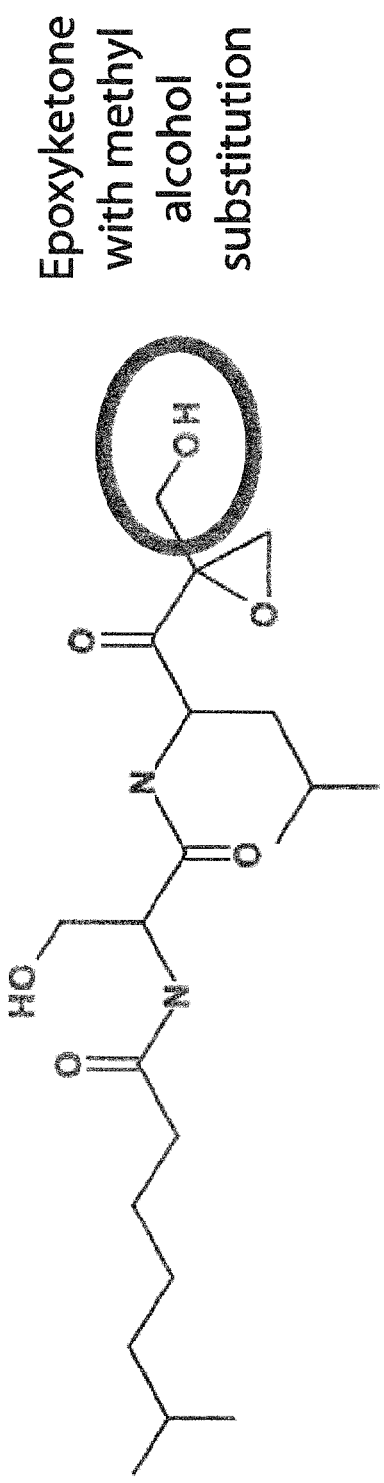
Figure 3:
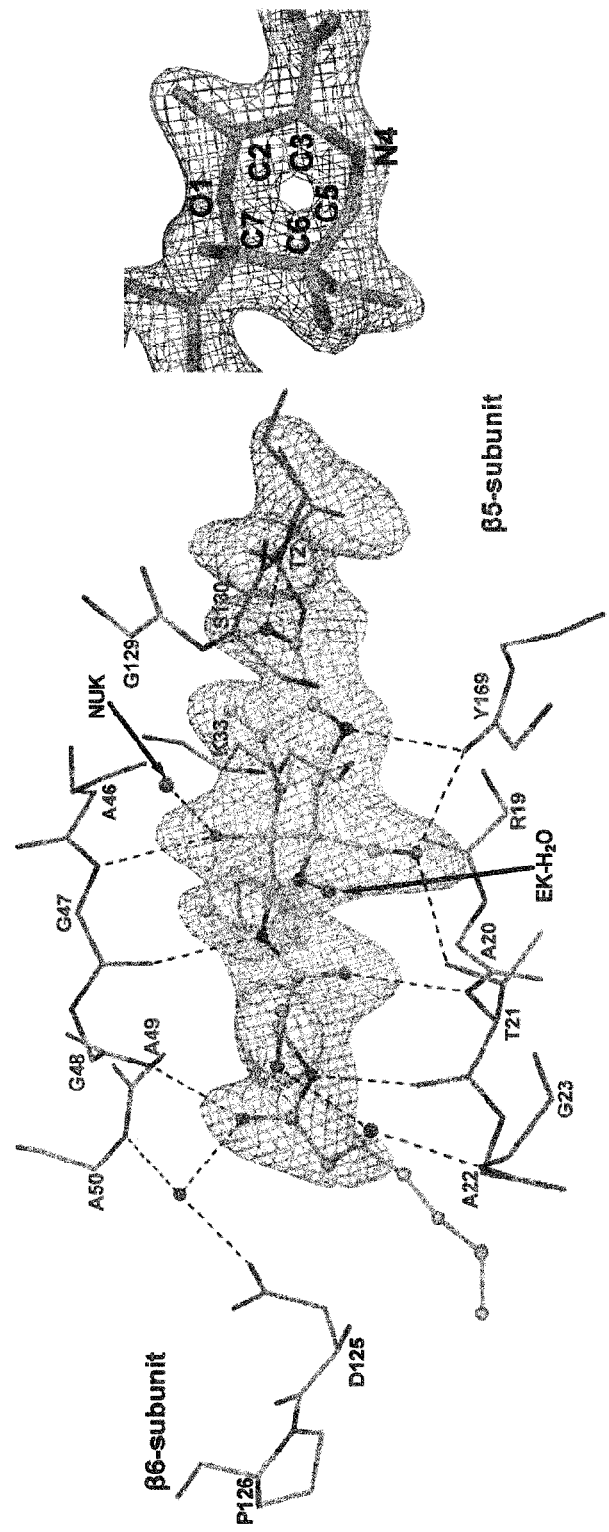

FIG. 3: Confirmation that a 7-membered 1,4-oxazepane ring structure is formed upon inhibition of proteasomes with epoxyketone inhibitors. Shown are the chemical structures of Oprozomib (top left) and dihydroeponemycin (top right). The oval highlights that Oprozomib contains a methyl group and dihydroeponemycin a methanolic group in the carbon atom in α-position to the ketone, respectively. The bottom panels illustrate the β5 active site inhibited with Oprozomib (bottom left) and Dihydroeponemycin (bottom right), along with an omit map contoured at 46 for the inhibitor, the cyclic linkage and β5Thr2. The main chain segments of β5 residues 2, 19-21, 33, 45-50, 129-131, 169,170 and β6 125,126 are indicated along with the β5 side chains of Thr2, Thr23, Lys33, Ser130 and the side chains of β6 Asp125, Pro126 as sticks. Dashed lines signify hydrogen bonds (≤3.2 Å distance). In the respective bottom right panels close-up views of the inhibitor-Thr1 linkages are shown along with an omit map contoured at 66. Note that the electron density map does not support a chiral center in the case of epoxomicin, which contains a methyl and a methanolic group, which would be a consequence of the proposed mechanism for 1,4-morpholine ring formation (bottom left) (Groll et al., loc. cit.). The dihydroeponemycin structure does not reveal electron density consistent with the presence of two methanolic groups, yet again disproving 1,4-morpholine ring formation (bottom right).

Figure 4:
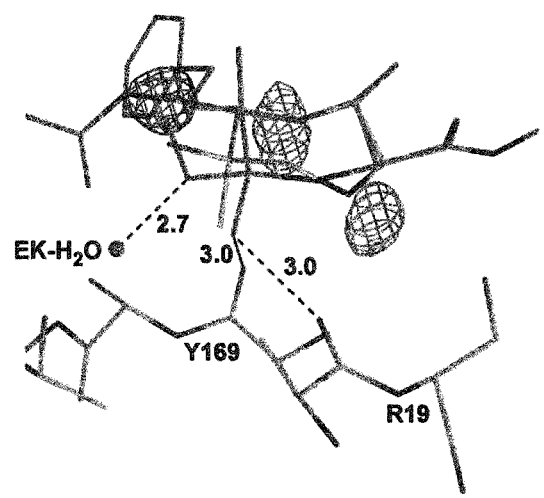

FIG. 4: Attempts to model a 1,4-morpholine ring structure in the linkage occurring between epoxyketone inhibitor and the proteasome active site Threonine1. Shown is an overlay of the proteasome active site (main chain) inhibited by a 1,4-oxazepane linkage and the attempted 1,4-morpholine linkage. The attempted 1,4-morpholine refinement reveals that a van-der-Waals clash occurs with the methyl group of the inhibitor and the main chain carbonyl atoms of R19 and Y169. Additionally, strong negative difference density at 5 sigma is visible at the C5 methanol atom of the 1,4-morpholine linkage. Positive densities are visible at positions 4 and 5 of the 1,4-oxazepane linkage. These findings entirely exclude formation of 1,4-morpholine ring formation in the epoxyketone inhibited proteasome active site.

Figure 5:
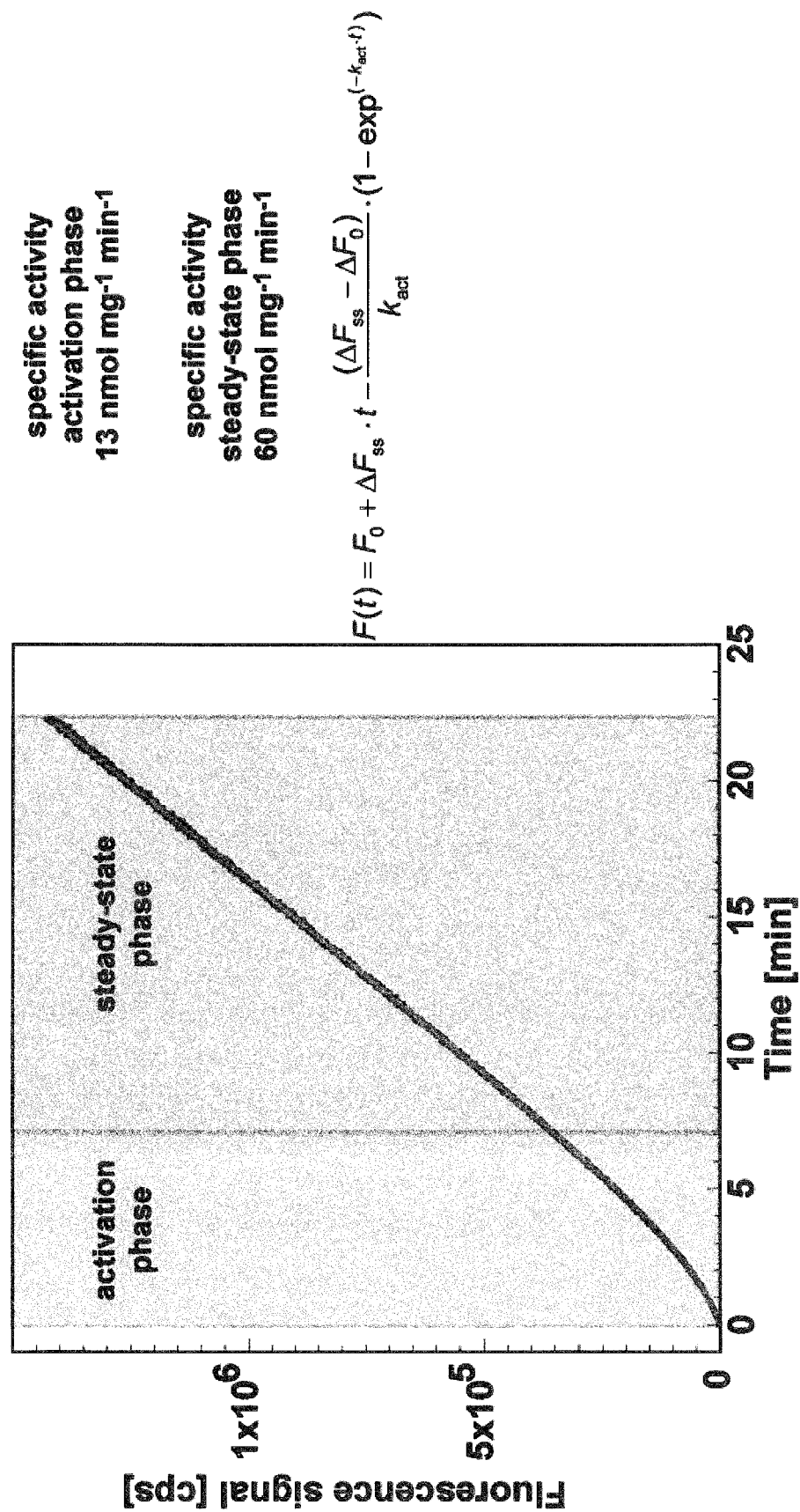

FIG. 5: Enzymatic characterization of proteasome catalytic activity. Measurements were performed as described in methods. The left panel depicts a typical kinetic experiment, where the increase in fluorescence signal of the AMC released by proteolytic cleavage is plotted against time. The left window signifies an activation phase in enzymatic peptide cleavage, whereas the right window represents the steady-state phase. In the right panel the specific activities for the human 20S proteasome purified by our method are indicated for the pre-steady-state (prior to activation) or and the steady-state phases, respectively. The equation shown in the right panel was used to perform fits against the experimental data. $F_0$ designates the initial fluorescence, $\Delta F_{ss}$: fluorescence increase in the steady-state part of the measurement, $k_{act}$: the rate constant. The exponential term with the rate constant $k_{at}$ is used to describe the activation phase of the reaction.

The examples illustrate the invention.

EXAMPLE 1

Crystallography

Initial phases for human 20S proteasomes were determined by molecular replacement using the murine 20S structure (PDB ID: 3UNE). The model was then optimized by several rounds of interactive manual model building in Coot and refinement in Refmac5. The obtained structures display excellent stereochemistry with typical values for $R_{work}$=18% and $R_{free}$=21%, reveal superb electron densities for all 6724 residues and reveal several ligands as present in buffers used for purification and crystallization.

Using a dataset to 1.8 Å resolution, we created a reference model. With the availability of this excellent model for the human 20S proteasome, now structure determination takes minutes by automated refinement of the reference model against integrated and scaled X-ray data from related crystals. Bound ligands can then be rapidly identified in difference density maps and modeled interactively in Coot.

Native crystals were soaked with the epoxyketone inhibitors shown in FIG. 1. Co-crystal structures of human 20S proteasomes in complex with these inhibitors at resolutions between 1.9-2.1 Å (0.3-0.5 Å better resolution than presently available structures) were solved. Surprisingly, after refinement of these co-crystal structures, which allow the modelling of all parts of human 20S proteasomes at atomic resolution, it was not possible to visualize the presumed 1,4-morpholine ring structure in the inhibited state. The electron density maps in the new epoxyketone/human 20S proteasome co-crystal structures in all cases did not agree with the formation of a 1,4-morpholine 6-ring. Instead, density for an additional atom became clearly visible, which is consistent with a 7-ring structure. In fact, modelling the cyclic molecule visible in the inhibited state formed by the reaction of the epoxyketone inhibitors with the active site catalytic threonine amino acid revealed that it represents a 1,4-oxazepane 7-ring structure (FIG. 2).

The observation of a 1,4-oxazepane structure contrasts with previously presumed chemical inhibition mechanisms of 20S proteasomes by epoxyketones. Therefore, a control experiment was performed to ensure that the observation of this 7-membered ring structure is true and the modelling of the 1,4-oxazepane structure in the inhibited proteasome active site is justified. Additionally, this control experiment should provide insight into the chemical inhibition mechanism by which the 7-ring structure is formed upon proteasome inhibition. For this control experiment, the co-crystal structures determined using the epoxyketone inhibitors epoxomicin and dihydroeponemycin were compared. Epoxomicin contains an epoxide group with a methyl ligand at the carbon atom, where the nucleophilic attack is presumed to occur in order to form the presumed 1,4-morpholine inhibited ring structure (FIG. 3, top left). Additionally, after formation of the presumed 1,4-morpholine structure ring opening of the epoxide at the carbon atom in α-position to the ketone should yield a stereo center, which contains both a methyl and a methanolic group (FIG. 3, right panel) (Groll et al., loc. cit.). Dihydroeponemycin in contrast already contains a methanolic ligand at the carbon atom, where the nucleophilic attack is presumed to occur in order to form the proposed 1,4-morpholine inhibited ring structure (FIG. 3, top right). As a consequence, after formation of the proposed 1,4-morpholine structure ring opening of the epoxide at the carbon atom in α-position to the ketone should yield a non-chiral center, which contains two methanolic groups. At the resolutions at which both co-crystal structures were determined (1.9 and 2.0 Å), it is possible to verify if this is the case. Surprisingly however, the electron density maps of both structures revealed that the inhibited state is formed by the covalent attack of the electrophilic carbon atom in β-position to the ketone (FIG. 3, bottom panels), excluding the possibility that a 1,4-morpholine ring structure is formed in the inhibited state by the absence of electron density compatible with a methanolic group in the case of epoxomicin and two methanolic groups in dihydroeponemycin.

Attempts to model the electron density in the active site of the dihydroeponemycin complex by a 1,4-morpholine ring structure linkage were unsuccessful (FIG. 4). 1,4-morpholine linkage refinement resulted in a severely distorted molecular geometry characterized by the elongation of the N4-carbon bonds by 0.1-0.2 Å, shortening of the C5-alcohol carbon bond by 0.1 Å and deviation of the methyl-C5-alcohol bond angle by −20 degrees off the expected value. Additionally, the methyl carbon exhibited a van-der-Waals distance of 3.0 Å to the Arginine 19 and Tyrosine 169 main chain oxygen atoms, which is too close. Moreover, strong negative difference density peaks in difference maps contoured at 5 sigma levels at the C5 methanol oxygen of the 1,4-morpholine ring model, as well as positive density peaks contoured at 4.5 sigma levels close to positions 4 and 5 of our 1,4-oxazepane ring model remained after this 1,4-morpholine ring refinement. In contrast, no residual difference (neither negative nor positive) density was present in the refined 1,4-oxazepane linkage in density maps contoured above 2.3 sigma.

EXAMPLE 2

Synthesis

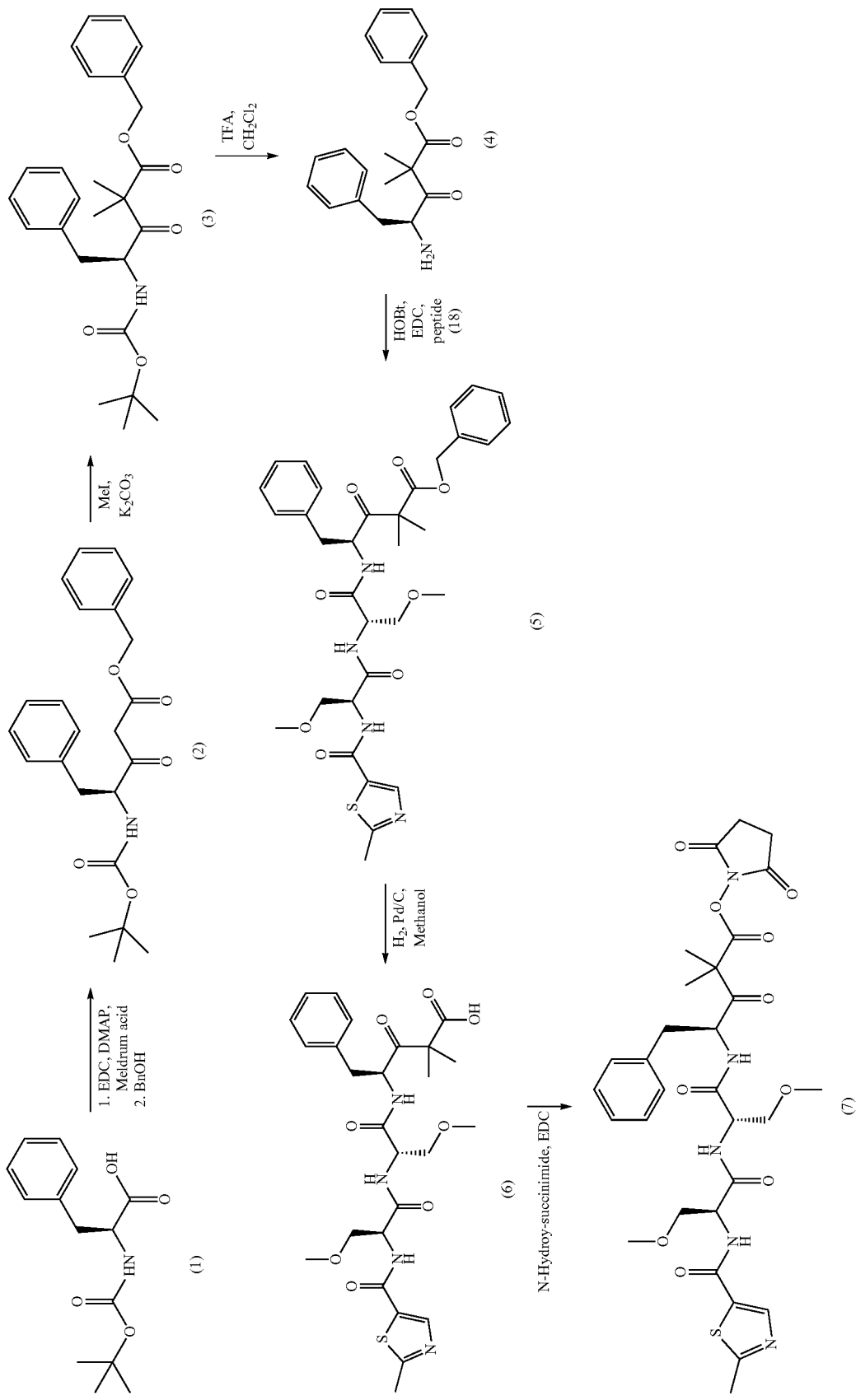

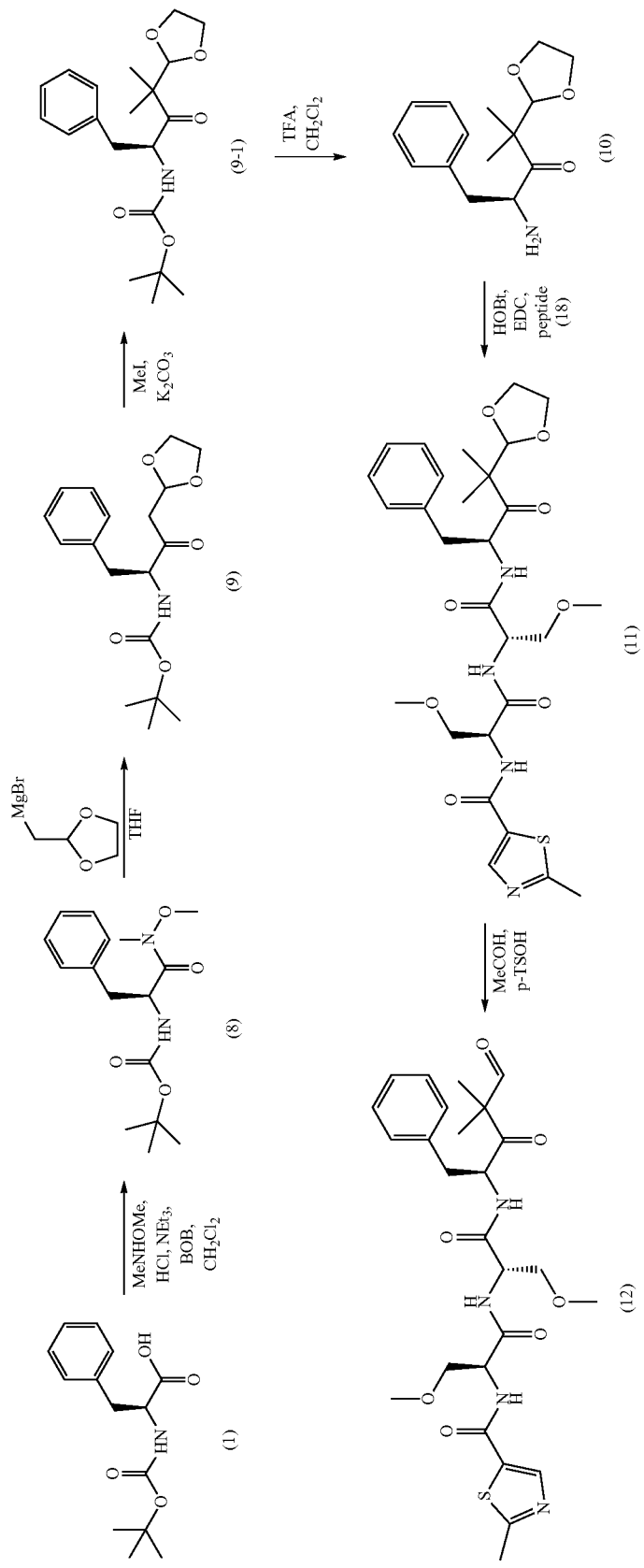

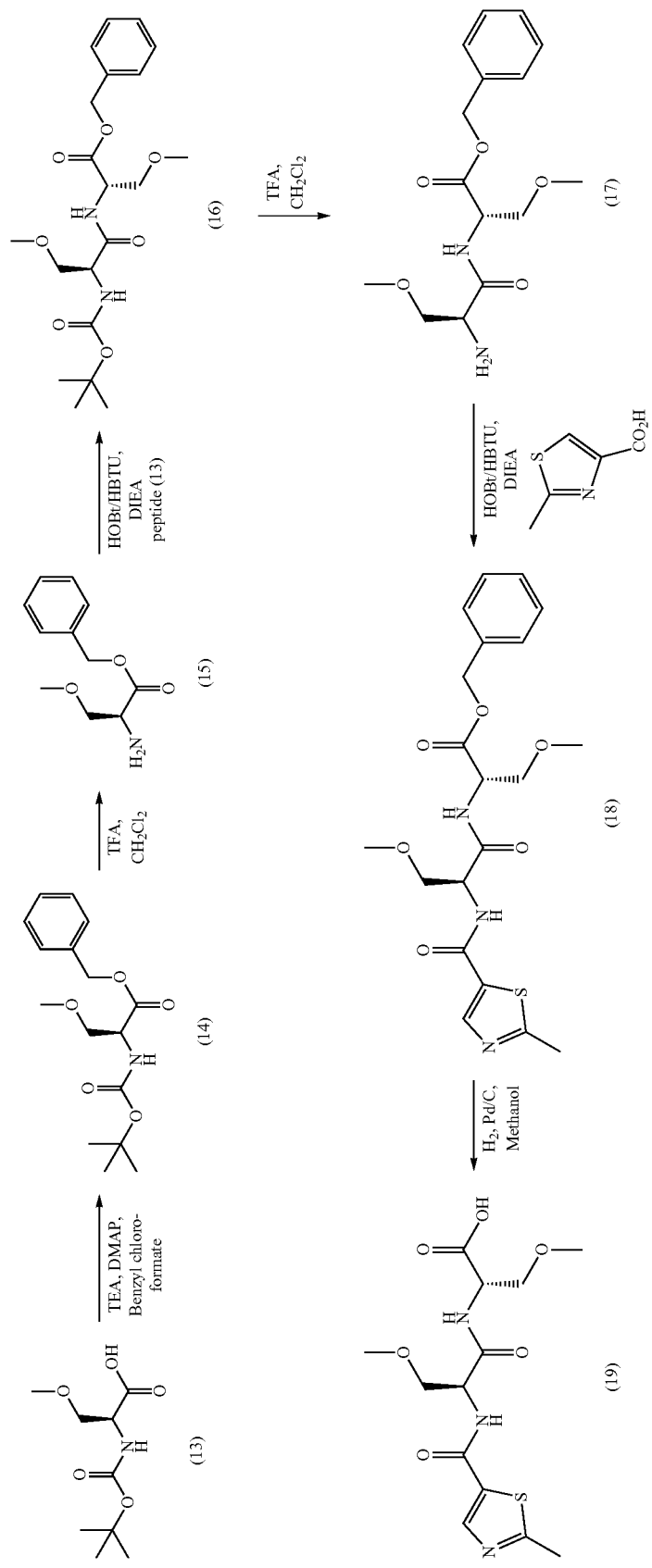
Scheme 5: Synthesis of tripeptide. Details are given below; see steps L to Q.

A) To a solution of N-Boc-L-Phenylalanine (1) in CH$_2$Cl$_2$ is added a EDC (1 eq.), DMAP (1 eq.) and Meldrum's acid (1 eq.). The reaction is stirred at room temperature for 17 hours, then poured into 1 M HCl. The layers are separated and the aqueous layer is extracted three times with CH$_2$Cl$_2$. The organic layers are combined, washed with brine, dried over MgSO$_4$ and concentrated in vacuum. The residue is heated to 80° C. in toluene and after the addition of benzyl alcohol (1 eq.) for 4 hours. The solvent is the removed in vacuum and the residue purified by flash chromatography and elution with ethyl acetate to yield (2).

B) A solution of (2), methyl iodide (3 eq.) and potassium carbonate (2 eq.) in acetone is heated under reflux for 17 hours. 2 volume equivalents of water are added and the resulting mixture extracted three times with 2 volume equivalents ethyl acetate. The organics are combined, dried over MgSO$_4$ and concentrated in vacuum. The residue is purified by preparative HPLC in 0.1% formic acid in water, with a gradient to 0.1% formic acid in acetonitrile to give (3).

C) A solution of (3) is stirred in a 10% TFA solution in CH$_2$Cl$_2$ for 17 hours at room temperature. The solvent is subsequently removed in vacuum to yield (4).

D) To (4) (1 eq.) in CH$_2$Cl$_2$ and triethylamine (0.001 eq.) is added (19) (1 eq.), HOBT (0.2 eq.) and EDC (2 eq.). The solution is stirred at 25° C. for 24 hours and then washed three times with saturated sodium hydrogencarbonate solution, once with deionized water and brine each, and the organic layer is dried over MgSO$_4$. The solvent is removed in vacuo and the residue purified by flash chromatography eluting with 1:1 ethyl acetate:n-hexane to yield (5).

E) (5) is stirred in methanol containing 10% Pd/C under a hydrogen atmosphere (1 atm). After 2 hours the mixture is filtered through celite and the solvent removed in vacuo to the product (6).

F) To (6) in CH$_2$Cl$_2$ is added, EDC (2 eq.) and N-Hydroxysuccinimide (2 eq.) and the mixture stirred for 2 hours. The solvent is then removed in vacuo and the residue purified by flash chromatography, eluting with 1:5 ethyl acetate:n-hexane to yield (7).

G) To a stirred solution of Boc-L-Phenylalanine in CH$_2$Cl$_2$ is added O,N-dimethylhydroxylamine hydrochloride (1 eq.), triethylamien (2 eq.) and BOP (1 eq.). After 3.5 hours the solution is diluted 4-fold with CH$_2$Cl$_2$ and washed three times with 3 M HCL, three times with saturated sodium hydrogencarbonate and three times with brine. The organic layer is then dried over MgSO$_4$, the solvent removed in vacuo and the residue purified by flash chromatography with 1:3 ethyl acetate:n-hexane to yield (8).

H) The Weinreb amide (8) in THF under an Argon atmosphere is cooled to 0° C. and 1,3-Dioxacyclopentyl-2-MgBromide (5 eq.) in THF added dropwise. The reaction is allowed to reach 25° C. and after 4 hours of stirring, is quenched with 1 M HCl forming a precipitate. The precipitate is removed by filtration and washed three times with ethyl acetate. The combined organics are then washed with brine, dried over MgSO$_4$ and the solvent removed in vacuum. The residue is then purified by flash chromatography using 1:4 ethyl acetate: n-hexane as an eluent to yield (9).

I) A solution of (9) is stirred in a 10% TFA solution in CH$_2$Cl$_2$ for 17 hours at room temperature. The solvent is subsequently removed in vacuum to yield (10).

J) To (10) (1 eq.) in CH$_2$Cl$_2$ and triethylamine (0.001 eq.) is added (19) (1 eq.), HOBT (0.2 eq.) and EDC (2 eq.). The solution is stirred at 25° C. for 24 hours and then washed three times with saturated sodium hydrogencarbonate solution, once with deionized water and brine each, and the organic layer is dried over MgSO$_4$. The solvent is removed in vacuo and the residue purified by flash chromatography eluting with 1:1 ethyl acetate:n-hexane to yield (11).

K) A solution of (11) and p-TsOH (0.1 eq.) in acetaldehyde (0.5 eq.) is stirred under an argon atmosphere at 15° C. for 23 hours. The solvent is then removed in vacuum and the residue purified by flash chromatography, eluting with 1:5 ethyl acetate:n-hexane to yield (12).

L) To a solution of Boc-methylserine (13) in DCM (Dichlormethane) TEA (Triethylamine) and DMAP (4-Dimethylaminopyridine) are added. The resulting solution is cooled to −5° C., and benzyl chloroformate is then slowly added via an addition funnel under an atmosphere of argon. The reaction is kept at the same temperature for 3 h and then diluted with brine. The layers are separated, and the aqueous layer is extracted with DCM. The organic layers are combined and dried over Na$_2$SO$_4$. The Na$_2$SO$_4$ is removed by filtration, and the volatiles are removed under reduced pressure. The resulting residue is purified by flash chromatography using a mixture of hexane and ethyl acetate to provide intermediate (14) as white solid.

M) To a 0° C. solution of intermediate (14) in DCM TFA (Trifluoroacetic acid) is added slowly via a funnel. The reaction is kept at the same temperature for 1 h, concentrated, and dried under high vacuum overnight. The resulting residual TFA salt (15) is used in the next step without further purification.

N) To a −5° C. mixture of aforementioned TFA salt (15), Boc-methylserine (13), HOBt (Hydroxybenzotriazole), and HBTU (2-(1H-benzotriazol-1-yl)-1,1,3,3-tetramethyluronium hexafluorophosphate) in THF (Tetrahydrofuran) (600 mL) is added DIEA slowly via an addition funnel. The reaction is kept at the same temperature for 4 h, followed by dilution with EtOAc (Ethylacetate) and brine. The layers are separated, and the aqueous layer is extracted with EtOAc (2×300 mL). The organic layers are combined and dried over Na$_2$SO$_4$. The Na$_2$SO$_4$ is removed by filtration, and the volatiles are removed under reduced pressure. The resulting residue is purified by flash chromatography using a mixture of hexane and ethyl acetate to provide dipeptide (16) as white solid.

O) To a 0° C. solution of aforementioned intermediate (16) in DCM was added TFA slowly via an addition funnel. The reaction is kept at the same temperature for 2 h, concentrated, and dried under high vacuum overnight. The resulting residual TFA salt (17) is used in the next step without further purification.

P) To a −5° C. mixture of TFA salt (17), 2-methylthiazole-5-carboxylic acid, HOBt, and HBTU in THF is added DIEA slowly. The reaction is kept at the same temperature for 4 h and then diluted with EtOAc and brine. The layers are separated, and the aqueous layer is extracted with EtOAc. The organic layers are combined and dried over Na$_2$SO$_4$. The Na$_2$SO$_4$ is removed by filtration, and the volatiles are removed under reduced pressure. The resulting residue is purified by flash chromatography using a mixture of hexane and ethyl acetate to provide benzyl ester (18) as white solid.

Q) (18) is stirred in methanol containing 10% Pd/C under a hydrogen atmosphere (1 atm). After 2 hours the mixture is filtered through celite and the solvent removed in vacuum to the product (19).

EXAMPLE 3

Proteasome Assays
Activity Measurement
Preferred In Vitro Assay.

All kinetic measurements were performed using a FluoroMax®-4 fluorescence spectrophotometer (Horiba Scientific). Succinyl-Leucine-Leucine-Valine-Tyrosine-7-amido-4-methylcoumarin (Suc-LLVY-AMC (SEQ ID NO: 1), Bachem) was used as substrate to determine the chymotryptic-like activity of the β5 catalytic active site of the human 20S proteasome (R. L. Stein, F. Melandri, L. Dick, Kinetic characterization of the chymotryptic activity of the 20S proteasome. Biochemistry 35, 3899-3908 (1996)). The fluorescence emission of hydrolyzed AMC was continuously monitored at 460 nm ($\lambda$ex=380 nM). The reaction temperature was kept at 37° C. for all measurements and the reaction buffer for enzymatic assays specified in Table S1 was used. Suc-LLVY-AMC (SEQ ID NO: 1) and inhibitors (such as Oprozomib, Dihydroeponemycin, Z-LLY-Ketoaldehyde; "Suc" designating Succinyl and "Z" designating Benzyloxycarbonyl) were dissolved in DMSO and stored at −80° C. until usage. The DMSO concentration did not exceed 2% (v/v) in any measurement. For kinetic characterization of Suc-LLVY-AMC (SEQ ID NO: 1) conversion, 0.035 mg/mL (50 nM) human 20S proteasome in reaction buffer was pre-incubated for 3 minutes at 37° C. The reaction was started by the addition of substrate and the fluorescence signal was measured continuously. For determination of the first-order rate constant of inhibition of the respective inhibitors, the reaction mixture containing reaction buffer, 150 µM substrate and either Oprozomib (50 µM), Dihydroeponemycin (50 µM) or Z-LLY-Ketoaldehyde (15 µM) were pre-incubated at 37° C. for 3 minutes. The reaction was then started by the addition of human 20S proteasome to a final concentration 50 nM. The fluorescence signal was measured continuously.

Data were analyzed and fitted with OriginPro 9.1 and KaleidaGraph 4.03. The equation shown in FIG. 5 was used to analyze the chymotryptic-like catalytic activity and catalytic activation of the 20S proteasome. For the determination of the first-order inactivation rate constants, equations were used that contained either two exponential terms in case of Z-LLY-Ketoaldehyde, or two exponential terms plus a linear term for epoxyketones (Oprozomib and Dihydroeponemycin). The first of the two exponential terms accounts for the catalytic activation, whereas the second exponential term represents the catalytic inactivation by inhibitory action. The linear term in case of the epoxyketones was used to account for the residual activity of the proteasome after inactivation.

Alternative Kinetic Assay.

Time point measurements of the activity assays are performed to acquire an initial tendency of inhibitor binding. Different concentrations of 20S proteasome are used for each active site: 0.05 mg/ml for CL (Chymotryptic-like activity) and PGPH (Peptidyl-glutamyl peptide hydrolyzing activity) and 0.075 mg/ml for TL (Tryptic-like activity). The final reaction volume is 30 µl/well. A total number of five repetitions are performed to obtain root mean square deviation (RMSD), including a blank and a 100% initial activity reaction. The steps are as follows.

(1) A master mix is prepared: Respective amount proteasome (according to PGPH, TL, or CL activity determination).

(2) Eppendorf tubes are prepared with the amount of the respective inhibitor to be analysed; e.g. 500 µM concentration of the ligand in 30 µl is 1.5 µl per assay of a 10 mM inhibitor stock solution.

(3) 28.5 µl of the master mix is added to each Eppendorf tube. This solution is incubated for 15 min at room temperature and transferred to the respective wells of the 96 well plates.

(4) Following incubation, 1 µl of a 7.5 mM stock solution of substrate for the caspase, chymotryptic or tryptic site is added, giving a final substrate concentration of 250 µM. The plate is centrifuged and incubated at RT for 1 h.

(5) 300 µl of buffer is added to the reaction and the remaining proteasome activity is subsequently recorded by fluorescence at Ex (Excitation wavelength) 360 nm-Em (Emission wavelength) 460 nm.

(6) The remaining activity is calculated using the blank and 100% initial activity.

Once proteasome inhibition is observed through the time point measurements, the half maximal inhibitory concentration ($IC_{50}$) measurements can be performed. The percentage of the remaining activities is then plotted against the log concentration of the respective inhibitor. The obtained data are fitted with a conventional statistical program, for example as described in: Groll M, Gallastegui N, Maréchal X, et al (2010) 20S Proteasome Inhibition: Designing Non-Covalent Linear Peptide Mimics of the Natural Product TMC-95A. ChemMedChem 5:1701-1705.

Reference for Assay: A description of an activity assay can be found in Gallastegui, N., & Groll, M. (2012). Analysing Properties of Proteasome Inhibitors Using Kinetic and X-Ray Crystallographic Studies. In Methods in Molecular Biology (Vol. 832, pp. 373-390). doi:10.1007/978-1-61779-474-2_26.

Cellular Assays.

A further example is the Z-Sensor Proteasome assay from Takara/Clontech. ZsProSensor-1 is a proteasome-sensitive fluorescent reporter. It is a fusion of a bright green fluorescent protein (Exmax=496 nm, Emmax=506 nm) with a degradation domain which targets the protein for rapid degradation by the proteasome. The cells emit green fluorescence when there is a drop in proteasome activity.

Alternative Methods:

Proteasome-Glo™ Chymotrypsin-Like, Trypsin-Like and Caspase-Like Cell-Based Assays (Promega).

GFP-Assay: Bence N, Bennett E, Kopito R, Deshaies R. Application and analysis of the GFP(u) family of ubiquitin-proteasome system reporters. Ubiquitin and Protein Degradation, Pt B. 2005; 399:481-490.

A cellular assay for the immunoproteasome is the following:

Fluorogenic in vitro assay (Immunoproteasome): (Basler, M., & Groettrup, M. (2012).

Immunoproteasome-Specific Inhibitors and Their Application. In Methods in Molecular Biology (Vol. 832, pp. 391-401). doi:10.1007/978-1-61779-474-2_27)

In order to test whether your IP inhibitor is cell permeable, the following method based on proteasome immuno-precipitation and in vitro activity assay can be used. The steps are as follows.

(1) Incubate cells for 2 h with desired concentration of IP inhibitors in cell culture media at 37° C. We normally use mouse splenocytes (one spleen per sample). As control, use an equal number of cells without inhibitor.

(2) Wash cells three times with PBS to remove unbound inhibitor.

(3) Lyse cells in 500 µl lysis buffer and incubate for 20 min on ice.

(4) Centrifuge the lysates for 10 min at 20,800×g to remove debris.

(5) Discard pellet and add 3 µl of polyclonal rabbit-anti-mouse proteasome antibody and 50 µl protein A microbeads to the supernatant and incubate for 30 min on ice.

(6) Insert μ column into magnet.
(7) Equilibrate μ column with 1 ml NET-TON buffer.
(8) Load lysate on μ column and discard flow through.
(9) Wash column twice with 1 ml NET-TON buffer and three times with NET-T buffer.
(10) Add 50 μl of a fluorogenic substrate and incubate column for 30 min at 37° C.
(11) Add 200 μl lysis buffer and collect eluate.
(12) Measure the fluorescence in 100 μl of the eluate (96-well plate, flat bottom, black). The fluorescence in the eluate corresponds to the activity of the retained proteasome in the column.

LacZ assay (Immunoproteasome); see Basler, M., & Groettrup, M. (2012). Immunoproteasome-Specific Inhibitors and Their Application. In Methods in Molecular Biology (Vol. 832, pp. 391-401). doi:10.1007/978-1-61779-474-2_27.

Numerous MHC-I restricted CD8+ T-cell epitopes have been described to be dependent on IP subunits. Investigating the processing of such T-cell epitopes can test specificity of IP inhibitors. In order to analyse the LMP7-selective inhibitor PR-957, we investigated the male HY-derived CTL-epitope UTY 246-254, which was reported to be LMP7 dependent. Therefore, we treated male splenocytes with PR-957 and detected MHC-I presented UTY 246-254 peptides with the help of UTY 246-254-specific T-cell hybridomas in lacZ assays.

(1) Remove spleen of one male and one female mouse and take up spleen in 5 ml RPMI 10% FCS.
(2) Make a single-cell suspension by pressing spleen through a grid.
(3) Centrifuge cells for 5 min at 347×g and discard supernatant.
(4) Lyse the erythrocytes by resuspending cells in 5 ml pre-warmed 1.66% (w/v) NH4Cl solution (in 15-ml tubes).
(5) Incubate for 2 min at room temperature.
(6) Fill up to 15 ml with RPMI 10% FCS and centrifuge cells for 5 min at 347×g and discard supernatant.
(7) Wash cells with 15 ml PBS, centrifuge cells for 5 min at 347×g, and discard supernatant.
(8) Take up cells in 5 ml RPMI 10% FCS and count cells using a Neubauer chamber.
(9) Incubate 10 7 splenocytes in 3 ml RPMI 10% FCS per well (6-well tissue culture plate).
(10) Add desired amounts of inhibitor. You need one well of male splenocytes without inhibitor for comparison of untreated and treated samples. For female splenocytes, you only need one well without inhibitor.
(11) Incubate overnight at 37° C.
(12) Harvest splenocytes, wash cells twice with 15 ml PBS, and count splenocytes.
(13) Resuspend cells in RPMI 10% FCS at $10^7$/ml.
(14) Use 96-well round-bottom tissue culture plate and add 150 μl per well to wells A1-D1. Make four serial threefold dilutions of splenocytes (100 μl/per well).
(15) Harvest T-cell hybridomas, count, and resuspend in RPMI 10% FCS at 10^6/ml. (We use the UTY 246-254-specific T-cell hybridoma (5).)
(16) Add 100 μl of T-cell hybridomas per well (A1-A4; B1-B4). Add to half of your samples (C1-C4; D1-D4) 100 μl RPMI 10% FCS as background control.
(17) Female splenocytes are used as negative control and untreated male splenocytes as positive control and for comparison. You can make an additional positive control adding synthetic peptide (we use UTY 246-254 peptide at a concentration of 10^-7 M) to female splenocytes.
(18) Incubate o/n at 37° C.
(19) Centrifuge plate at 541×g for 90 s and discard supernatant.
(20) Add 100 μl lacZ buffer and incubate at 37° C.
(21) Measure absorbance at 570/620 nm when colour change is visible (approx. after 1-3 h).

EXAMPLE 4

Alternative Synthesis
Synthesis of Tripeptide 28584

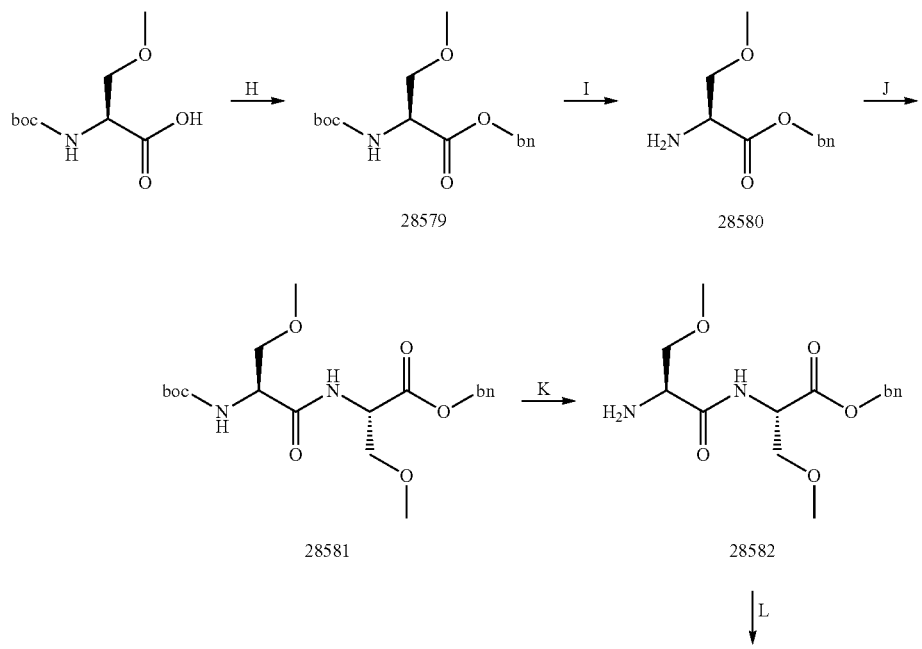

Scheme 6: Synthesis route of tripeptide 28584.

-continued

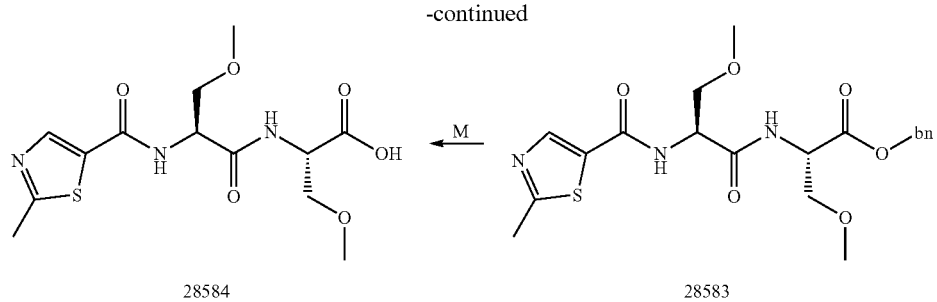

The synthesis of the tripeptide 28584 was successfully carried out according to the literature procedure. The formation of the Benzylester 28579 was performed in 4 g scale and 4.6 g product was obtained (>95% purity by ¹H-NMR, 98% purity by LC/MS, 82% yield). The following Boc-deprotection of 28579 led to 4.8 g of 28580 in quant. yield and 95% purity by 1H-NMR and 86% purity by LC/MS.

The peptide coupling was performed on a 2 g scale and 1.8 g of 28581 was obtained (95% purity by LC/MS, 90% purity by ¹H-NMR, 73% yield).

Synthesis of 28582 was carried out in 1.7 g scale and 1.7 g product (28582) was obtained as TFA salt (quant. yield, 90% purity by ¹H-NMR).

After amide formation of 2-Methyl-5-thiazolecarboxylic acid with 28582, 1.5 g of 28583 was obtained (80% yield, 93% purity by ¹H-NMR; >95% by LC/MS).

The benzyl ester deprotection of 28583 with 10% Pd/C was performed on 1.5 g scale and 1.0 g 28584 was obtained (79% yield, 95% purity by ¹H-NMR and LC/MS). It was found out that the benzyl ester deprotection requires more than catalytic amount 10% Pd/C. For fast deprotection at least equal amount of Pd/C is needed compared to the used amount of 28583.

Synthesis of NHS-Ketoester 28880 and Thioester 29502, 29865

Scheme 7: Synthesis of NHS-Ketoester 28880 or thioester 29502 and 29865.

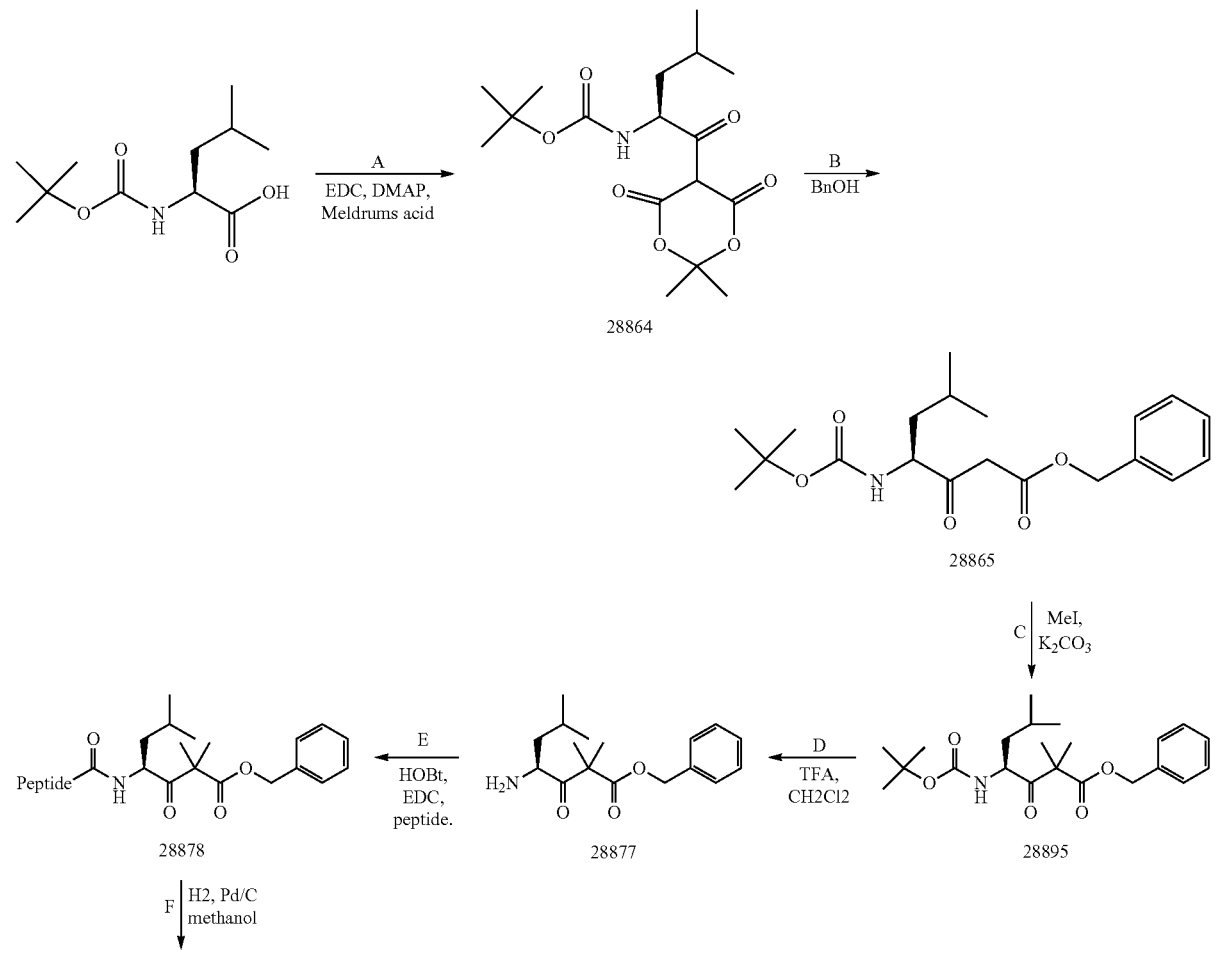

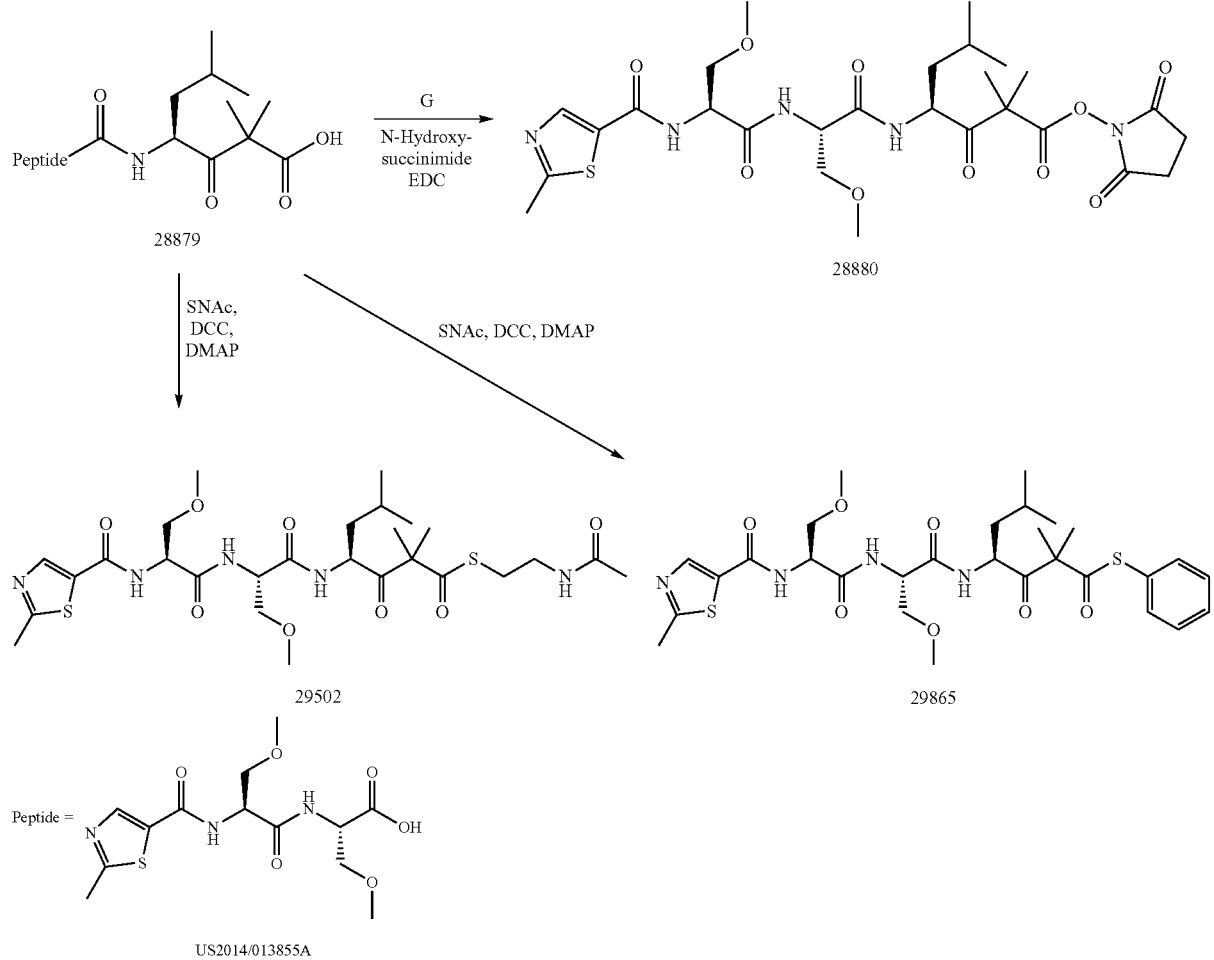

The formation of the Meidrum's acid intermediate 28864 was performed by using N-Boc-L-Leu-OH and EDC/DMAP in DCM as reported in the literature. It was observed that under those reaction conditions product with complex mixture of side products was formed. One major side product was identified by LC/MS as cyclized Leucine derivative. The reaction crude has a purity of approx. 30-40% determined by $^1$H-NMR.

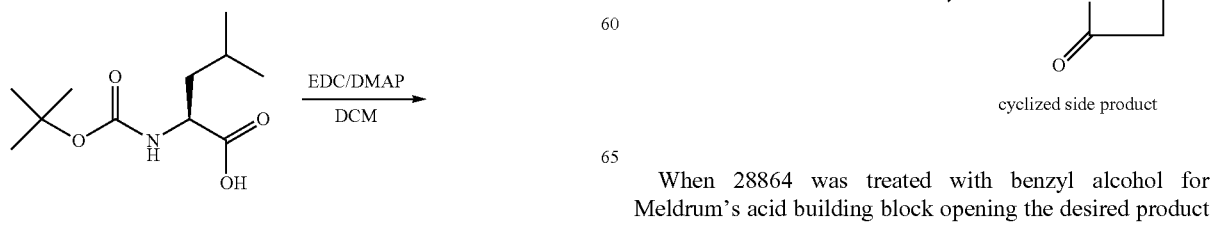

Scheme 8: Reaction of N-Boc—L-Leu-OH to 28864 and the formation of observed cyclized side product.

When 28864 was treated with benzyl alcohol for Meldrum's acid building block opening the desired product 28865 was obtained. From 6.7 g reaction 1.7 g of 28865 was obtained (26% yield, 85% purity by $^1$H-NMR).

The double alkylation of 28865 was carried out by using excess of methyl iodide in the presence of K2CO3 in acetone which led to the formation of 28895 in 30-38% yield. In the end, out of a 3.7 g scale reaction 1.3 g of 28895 was obtained (38% yield, 95% purity by $^1$H-NMR).

The N-Boc deprotection of 28877 was performed using 10% TFA in DCM and was done as reported in the literature. After work up $^1$H-NMR clearly showed the mixture of compounds.

Another reaction was carried out and it was found out that the reaction was completed in two hours instead of 17 h which was reported in the literature.

The reaction mixture was concentrated at room temperature.

The deprotection was performed shortly before the amide coupling of 28878. 400 mg reaction of 28877 was carried out and the reaction crude (purity 85% by LC/MS) was used immediately for the next reaction step.

HATU was used as a coupling reagent for the synthesis of 28878 successfully. After work up the $^1$H-NMR indicated that epimerization was occurred (15% by $^1$H-NMR). This is corresponding to the reported literature. The synthesis of 28878 was successfully performed in a 100 mg and 300 mg scale by using HATU as coupling reagent. After purification 65 mg (36% yield, purity 95% by LC/MS) and 298 mg (55% yield, purity 95% by LC/MS) product 28878 was obtained. In both cases the presence of epimer was decreased from 15 mol % to 8 mol %.

The synthesis of 28879 was performed using N,N-dicyclohexylcarbodiimide and N-hydroxysuccinimide in THF/DMF as solvent system. By LC/MS the formation of a peak with the right mass was observed.

After precipitation of dicyclohexylurea in DCM and removal of excess of NHS by washing with water, 25 mg were obtained (48% purity by LC/MS). The crude compound was tried to purify by preparative HPLC on reverse phase column. The fractions were extracted by DCM in order to avoid hydrolysis/decarboxylation. 0.7 mg with 93% purity and a peak with the right product mass in LC/MS was obtained. $^1$H-NMR in CDCl3 provided no clear indication due to the small amount of sample.

For structure elucidation, reaction of 28880 was performed on a 140 mg scale by using N,N-dicyclohexylcarbodiimide and N-hydroxysuccinimide (NHS) in EtOAc/DMF as solvent system. LC/MS analysis showed the formation of a peak with the right product mass. After precipitation of dicyclohexylurea in DCM and removal of excess of NHS by washing with water, 120 mg were obtained (48% purity by LC/MS). The crude was tried to purify by preparative HPLC.

To enhance the coupling efficiency PyBOP was used as a coupling reagent. By using 1.3 eq. of PyBOP, 2.0 eq. DIPEA and 3.0 eq. NHS a very prominent peak with right product mass was observed also in much higher intensity than before.

In order to prove whether the peak with the right product mass observed in LC/MS is an artefact or belongs to the desired compound 28880, it was treated with MeOH to form the methylester of 28880. LC/MS analysis showed that the peak with the mass of the expected NHS-ester was disappeared and the formation of a peak with the right mass of the methylester was observed.

Purification was done by doing two times short plug filter column chromatography. In the first case the reaction mixture was directly filtered through a pad of silica without any solvent removal after the reaction. THE was used as eluent. After concentration of this above mentioned fraction, compound was purified again by short column chromatography using DCM/THF mixture as eluent. 9.8 mg of product was obtained (62% purity by LC/MS). Due to very small amount the purity of product cannot be improved further. However, $^1$H-NMR is corresponding to the product. For larger scale the purification was improved by optimizing the column chromatography using c-hexane/THF as solvent mixture.

Another 100 mg reaction was performed by using 1.3 eq. of PyBOP, 2.0 eq. DIPEA and 3.0 eq. NHS as coupling conditions. Purification was done by doing short plug filter column chromatography. In the first case the reaction mixture was filtered through a pad of silica without any concentration. THF was used as eluent. After concentration of the above mentioned fraction, compound was purified by column chromatography using c-hexane/THF mixture as eluent. 47 mg of desired title compound 28880 was obtained with purity of 88% by $^1$H-NMR, containing 13.5 mol % of decarboxylated 28879.

In conclusion, 47 mg of 28880 was delivered successfully in 88% purity by $^1$H-NMR.

The invention claimed is:

1. A compound of formula (I)

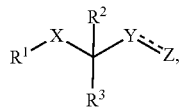

wherein
X is C=O, C=S or B—OH;
Y is an electrophile and Z is a leaving group, or Y=Z is an electrophile;
$R^1$ is a peptidic group, wherein said peptidic group consists of three α-amino acids and wherein
(a) the N-terminal amino acid is selected from Ser(OMe), Leu, Phe and Ala; the middle amino acid is selected from Ser(OMe), Leu, Phe and Ala; and/or the C-terminal amino acid is attached to X and is a truncated amino acid residue that lacks a carbonyl group, wherein the truncated amino acid residue is based upon an amino acid selected from Phe, Tyr, Leu, Ser(OMe) and Ala; or
(b) said peptidic group consists of Ser(OMe)-Ser(OMe)-Phe, Leu-Leu-Tyr or Ala-Ala-Ala
$R^2$ and $R^3$ are independently selected from H, methyl, methoxy, ethyl, ethenyl, ethynyl and cyano, wherein methyl and ethyl may be substituted with OH or halogen.

2. The compound of claim 1, wherein Y=Z is
(a) CH=O, $CH_2$—I, $CH_2$—Br, $CH_2$—Cl, $CH_2$—OPO$(OH)_2$, $CH_2$-OTs, CO—NHS or CH=$CH_2$, wherein OTs is p-toluene sulfonyloxy and NHS is N-oxy-succinimide; or
(b) O—I, O—Br, O—Cl, S—I, S—Br or S—I.

3. The compound of claim 1, wherein $R^2$ and $R^3$ are identical.

4. The compound of claim 1, wherein X is C=O and Y=Z is CH=O or CO—NHS.

5. A method of inhibiting a proteasome, said method comprising bringing into contact a proteasome and a compound as defined in claim 1.

6. A method of treating, ameliorating or preventing cancer, an autoimmune disease, muscular dystrophy, emphysema, or cachexia accompanying cancer or AIDS, comprising administering a compound as defined in claim 1 to a subject in need thereof.

7. The method of claim 6, wherein
(a) said cancer is a lymphoid malignancy, wherein the lymphoid malignancy is multiple myeloma (MM) or non-Hodgkin lymphoma, wherein the non-Hodgkin lymphoma is a B-cell lymphoma selected from mantle cell lymphoma (MCL), diffuse large B-cell lymphoma (DLBCL), and Waldenström macroglobulinaemia; or
(b) said autoimmune disease is rheumatoid arthritis, systemic lupus erythematosus, Sjörgen's syndrome or scleroderma.

8. The compound of claim 3, wherein $R^2$ and $R^3$ are selected from methyl, methoxy, and —$CH_2OH$.

* * * * *